United States Patent [19]
Betts et al.

[11] Patent Number: 5,447,925
[45] Date of Patent: Sep. 5, 1995

[54] ANTIBIOTIC COMPOUNDS

[75] Inventors: Michael J. Betts, Wilmslow; Gloria A. Breault, Congleton, both of England

[73] Assignees: Imperial Chemical Industries PLC, London, United Kingdom; ICI Pharma S.A., Cergy Cedex, France

[21] Appl. No.: 129,148

[22] Filed: Oct. 6, 1993

[30] Foreign Application Priority Data

Apr. 8, 1991 [GB] United Kingdom ............... 9107342

[51] Int. Cl.$^6$ .................. C07D 487/00; A01N 43/00; A61K 31/395
[52] U.S. Cl. ................................. 514/210; 540/350
[58] Field of Search ......................... 540/350; 514/210

[56] References Cited

U.S. PATENT DOCUMENTS 4,963,544  10/1990  Murata et al.
5,194,624   3/1993  Murata et al.
5,215,983   6/1993  Murata et al.

FOREIGN PATENT DOCUMENTS 182213  5/1986  European Pat. Off.
280771  9/1988  European Pat. Off.
472062  2/1992  European Pat. Off.

*Primary Examiner*—Johann Richter
*Assistant Examiner*—Rebecca Cook
*Attorney, Agent, or Firm*—Cushman Darby & Cushman

[57] ABSTRACT

The present invention provides a compound of the formula (I)

wherein:
$R^1$ is 1-hydroxyethyl, 1-fluoroethyl or hydroxymethyl;
$R^2$ is hydrogen or $C_{1-4}$alkyl;
n is zero or an integer 1 to 4; and
P is a benzene ring substituted by groups $R^3$ and $R^4$ which are ortho with respect to one another wherein $R^3$ and $R^4$ are independently hydroxy or in vivo hydrolysable esters thereof;
or P is a group of the formula (II) or (III)

wherein
M is oxygen or a group $NR^5$ wherein $R^5$ is hydrogen or $C_{1-4}$alkyl;
ring P being optionally further substituted;
or a pharmaceutically acceptable salt or in vivo hydrolysable ester thereof.

12 Claims, No Drawings

ANTIBIOTIC COMPOUNDS

This application is a 371 of PCT/GB92/00587 filed Apr. 2, 1992.

The present invention relates to carbapenems and in particular to such compounds containing a dihydroxybenzene or related group. This invention further relates to processes for their preparation, to intermediates in their preparation, to their use as therapeutic agents and to pharmaceutical compositions containing them. The compounds of this invention are antibiotics and can be used in the treatment of any disease that is conventionally treated with antibiotics for example in the treatment of bacterial infection in mammals including humans.

Carbapenems were first isolated from fermentation media in 1974 and were found to have broad spectrum antibacterial activity. Since this discovery substantial investigations have been made into new carbapenem derivatives and many hundreds of patents and scientific papers have been published.

The first, and so far the only, carbapenem to be commercially marketed is imipenem (N-formimidoyl thienamycin). This compound has a broad spectrum of antibacterial activity.

The present invention provides compounds with particularly good antibacterial activity in particular against strains of Pseudomonas aeruginosa and those strains of this organism which have been shown to be resistant to imipenem. They exhibit good stability to beta-lactamases. In addition many of the compounds of this invention exhibit favourable pharmacokinetics.

The carbapenem derivatives referred to herein are named in accordance with the generally accepted semi-systematic nomenclature:

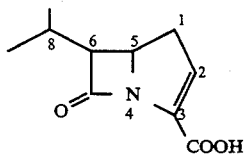

Accordingly the present invention provides a compound of the formula (I)

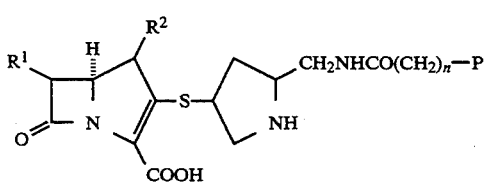

wherein:
R$^1$ is 1-hydroxyethyl, 1-fluoroethyl or hydroxymethyl;
R$^2$ is hydrogen or C$_{1-4}$alkyl;
n is zero or an integer 1 to 4; and
P is a benzene ring substituted by groups R$^3$ and R$^4$ which are ortho with respect to one another wherein R$^3$ and R$^4$ are independently hydroxy or in vivo hydrolysable esters thereof;
or P is a group of the formula (II) or (III)

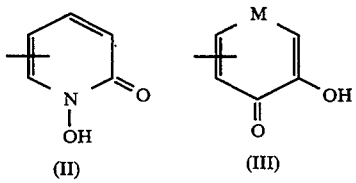

wherein
M is oxygen or a group NR$^5$ wherein R$^5$ is hydrogen or C$_{1-4}$alkyl;
ring P being optionally further substituted;
or a pharmaceutically acceptable salt or in vivo hydrolysable ester thereof.

Preferably R$^1$ is 1-hydroxyethyl.

R$^2$ is hydrogen or C$_{1-4}$alkyl for example methyl, ethyl, n-propyl, isopropyl and n-butyl. Preferably R$^2$ is hydrogen or methyl and in particular R$^2$ is methyl.

n is zero or an integer 1 to 4. Suitably n is 1 to 4 for example methylene or ethylene. Preferably n is zero.

In one aspect P is a ring of the formula (II). In another aspect P is a ring of the formula (III). Suitably M is oxygen thus forming a pyranone ring. In an alternative aspect M is —NR$^5$— wherein R$^5$ is hydrogen or C$_{1-4}$alkyl for example methyl or ethyl. Preferably R$^5$ is hydrogen thus forming a 3,4-dihydroxypyridine ring.

In a preferred aspect P is a benzene ring. R$^3$ is hydroxy or an in vivo hydrolysable ester thereof. R$^4$ is hydroxy or an in vivo hydrolysable ester thereof.

In vivo hydrolysable esters are those pharmaceutically acceptable esters that hydrolyse in the human body to produce the parent hydroxy or carboxy compound. Such esters can be identified by administering, eg. intravenously to a test animal, the compound under test and subsequently examining the test animal's body fluids. Suitable in vivo hydrolysable esters for hydroxy include acetoxy, propionyloxy, pivaloyloxy, C$_{1-4}$alkoxycarbonyloxy for example ethoxycarbonyloxy, phenylacetoxy and phthalidyl. Suitable in vivo hydrolysable esters for carboxy include C$_{1-6}$alkoxymethyl esters for example methoxymethyl; C$_{1-6}$alkanoyloxymethyl esters for example pivaloyloxymethyl; C$_{3-8}$cycloalkoxycarbonyloxyC$_{1-6}$alkyl, for example 1-cyclohexyloxycarbonyloxyethyl; 1,3-dioxolen-2-onylmethyl esters for example 5-methyl,1,3-dioxolen-2-onylmethyl; phthalidyl esters and C$_{1-6}$alkoxycarbonyloxyethyl esters for example 1-ethoxycarbonyloxyethyl and may be formed at any carboxy group in the compound of this invention.

Conveniently R$^3$ and R$^4$ have the same value and are both hydroxy or are both in vivo hydrolysable esters, for example they are both acetoxy or pivaloyloxy.

As stated hereinbefore ring P is optionally further substituted. Particular optional substituents include C$_{1-4}$alkyl for example methyl, ethyl or isopropyl; halo for example chloro, bromo or fluoro; hydroxy; hydroxy C$_{1-4}$alkyl for example hydroxymethyl or hydroxyethyl; amino; nitro; C$_{1-4}$alkoxy for example methoxy or ethoxy; carboxyC$_{1-4}$alkyl for example carboxymethyl or carboxyethyl; C$_{1-4}$alkanoylamino for example acetamido; N-alkyl-N-C$_{1-4}$alkanoylamino; trifluoromethyl; carboxy; carbamoyl; C$_{1-4}$alkylcarbamoyl for example methylcarbamoyl; di-C$_{1-4}$alkylcarbamoyl for example di-[N-methyl]carbamoyl; cyano; C$_{1-4}$alkanesulphonamido for example methanesulphonamido; C$_{1-4}$alkanoyl for example acetyl; C$_{1-4}$alkanoyloxy for example acetoxy or propionoxy; $C_{1-4}$alkoxycarbonyl for example methoxycarbonyl; $C_{1-4}$alkylthio for example methylthio, $C_{1-4}$alkanesulphinyl for example methanesulphinyl; $C_{1-4}$alkanesulphonyl for example methanesulphonyl; $C_{2-4}$alkenyl for example allyl or vinyl; hydroxyiminomethyl (HON=CH—); $C_{1-4}$alkoxyiminomethyl for example methoxyiminomethyl; aminosulphonyl; N-$C_{1-4}$alkylaminosulphonyl for example N-methylaminosulphonyl; and di-[N-$C_{1-4}$alkyl]aminosulphonyl for example di-[N-methyl]aminosulphonyl.

Favoured optional substituents for ring P are fluoro, bromo, chloro, cyano, nitro, carboxy, carboxymethyl, hydroxy, di-[N-methyl]-carbamoyl, methanesulphonyl, di-[N-ethyl]aminosulphonyl and methoxycarbonyl.

The skilled man will realise that when P is a benzene ring up to 3 optional substituents, which may be the same or different, are possible. When P is a ring of formula (II) or (III) up to 2 or 3 optional substituents, which may be the same or different, are possible. In general we prefer up to 2 optional substituents.

The present invention covers all epimeric, diastereoisomeric and tautomeric forms of the compounds of the formula (I) except where otherwise indicated. In the formulae herein; a bond represented as a wedge indicates that in 3-D the bond would be coming forward out of the paper and a bond represented as hatched would be going back into the paper. The compounds of the formula (I) have a number of centres of optical activity, namely: within the group $R^1$ (when $R^1$ is 1-hydroxyethyl or 1-fluoroethyl); at the 6-position; at the 1-position (when $R^2$ is $C_{1-4}$alkyl); and at the 2' and 4' positions in the pyrrolidine ring:

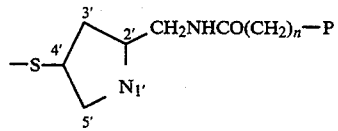

Preferred compounds are those in which the beta-lactam protons are in trans configuration with respect to one another. When $R^1$ is 1-hydroxyethyl or 1-fluoroethyl it is preferred that the 8-substituent has the R-configuration. Thus a preferred class of compounds is that of the formula (IA):

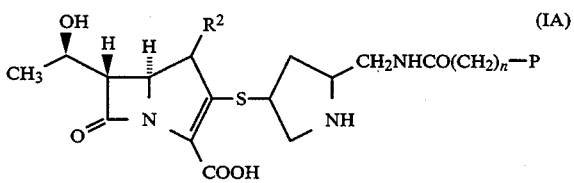

and pharmaceutically acceptable salts and in vivo hydrolysable esters thereof, wherein $R^2$, n and P are as hereinbefore defined.

When $R^2$ is $C_{1-4}$alkyl for example methyl it is preferred that the compound is in the form of the 1R configuration.

A particularly preferred class of compounds of the present invention is that of the formula (IV):

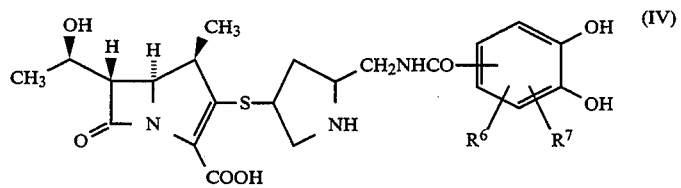

wherein $R^6$ and $R^7$ are independently hydrogen, halo, cyano, nitro, carboxy, carboxymethyl, hydroxy, methoxy, methoxyiminomethyl methanesulphonyl, di-[N-methyl]carbamoyl and di-[N-ethyl]aminosulphonyl. Preferably the benzene ring is substituted by the hydroxy groups in positions 3 and 4 relative to the amido linking group. Particular substitution patterns for the benzene ring include: 3,4-dihydroxybenzene, 3,4-dihydroxy-5-bromo-benzene, 2,5-dichloro- 3,4-dihydroxybenzene, 3,4,5-trihydroxybenzene, 3,4-dihydroxy-6-methoxycarbonylbenzene 3,4-dihydroxy-6-carboxybenzene, 3,4-dihydroxy-5-cyanobenzene, 3,4-dihydroxy-6-cyanobenzene, 3,4-dihydroxy-5-methanesulphonylbenzene, 3,4-dihydroxy-6-di[N-ethyl]aminosulphonylbenzene and 3,4-dihydroxy-6-di[N-methyl]carbamoylbenzene.

Particular compounds of the present invention are
(5R,6S,8R,2'S,4'S)-2-(2-(3,4-dihydroxybenzoylaminomethyl)pyrrolidin-4-ylthio)-6-(1-hydroxyethyl)carbapenem-3-carboxylic acid;
(5R,6S,8R,2'S,4'S)-2-(2-(5-bromo-3,4-dihydroxybenzoylaminomethyl)pyrrolidin-4-ylthio)-6-(1-hydroxyethyl)carbapenem-3-carboxylic acid;
(1R,5R,6S,8R,2'S,4'S)-2-(2-(5-cyano-3,4-dihydroxybenzoylaminomethyl)pyrrolidin-4-ylthio)-6-(1-hydroxyethyl)-1-methyulcarbapenem-3carboxylic acid;
(1R,5R,6S,8R,2'S,4'S)-2-(2-(5-hydroxy-3,4-dihydroxybenzoylaminomethyl)pyrrolidin-4-ylthio-6-(1-hydroxyethyl-1-methylcarbapenem-3-carboxylic acid;
(1R,5R,6S,8R,2'S,4'S)-2-(2-(6-carboxy-3,4-dihydroxybenzoylaminomethyl)pyrrolidin-4-ylthio)-6-(1-hydroxyethyl)-1-methylcarbapenem-3-carboxylic acid;
(1R,5R,6S,8R,2'S,4'S)-2-(2-(5-methylsulphonyl-3,4-dihydroxybenzoylaminomethyl)pyrrplidin-4-ylthio)-6-(1-hydroxyethyl)-1methylcarbapenem-3-carboxylic acid;
(1R,5R,6S,8R,2'S,4'S)-2-(2-(6-di-(N-methyl)carbamoyl)-3,4-dihydroxybenzoylaminomethyl)pyrrolidin-4-ylthio)-6-(1-hydroxyethyl)-1-methylcarbapenem-3-carboxylic acid;
(1R,5R,6S,8R,2'S,4'S)-2-(2-(6-cyano-3,4-dihydroxybenzoylaminomethyl)pyrrolidin-4-ylthio)-6-(1-hydroxyethyl)-1-methylcarbapenem-3carboxylic acid;
(1R,5R,6S,8R,2'S,4'S)-2-(2-(3,4-dihydroxybenzoylaminomethyl)pyrrolidin-4-ylthio)-6-(1-hydroxyethyl)-1-methylcarbapenem-3-carboxylic acid;
(1R,5R,6S,8R,2'S,4'S)-2-(2-(4,5-dihydroxypyridin-2-ylcarbonylamino-methyl)pyrro -4-ylthio)-6-(1-hydroxyethyl)-1-methylcarbapenem-3-carboxylic acid.

Suitable salts include acid addition salts such as hydrochloride, hydrobromide, citrate, maleate and salts formed with phosphoric and sulphuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids, for example, lysine.

For the avoidance of doubt there may be two or three salt forming counter ions depending on the number and type of charged functions and the valency of the counter ions.

In order to use a compound of the present invention or a pharmaceutically acceptable salt or in vivo hydrolysable precursor thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or in vivo hydrolysable precursor thereof and a pharmaceutically acceptable carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, emulsions, dispersible powders, suppositories and sterile injectable aqueous or oily solutions or suspensions.

In addition to the compounds of the present invention the pharmaceutical composition of this invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenecid) and inhibitors of metabolising enzymes (for example inhibitors of dehydropeptidases, for example Z-2-acylamino-3-substituted propenoates such as cilastatin) and N-acylated amino acids (for example see EP-A-178911).

A suitable pharmaceutical composition of this invention is one suitable for oral administration in unit dosage form, for example a tablet or capsule which contains between 100 mg and 1 g of the compound of this invention.

A preferred pharmaceutical composition of the invention is one suitable for intravenous, subcutaneous or intramuscular injection, for example a sterile injectable containing between 1 and 50% w/w of the compound of this invention.

The pharmaceutical compositions of the invention will normally be administered to man in order to combat infections caused by bacteria, in the same general manner as that employed for imipenem due allowance being made in terms of dose levels for the potency of the compound of the present invention relative to the clinical use of imipenem. Thus each patient will receive a daily intravenous, subcutaneous or intramuscular dose of 0.05 to 5 g., and preferably 0.1 to 2.5 g., of the compound of this invention, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a suitable daily oral dose is 0.5 to 5 g. of the compound of this invention, the composition being administered 1 to 4 times per day.

In a further aspect the present invention provides a process for preparing the compounds of the formula (I) or a pharmaceutically acceptable salt or in vivo hydrolysable ester thereof which process comprises deprotecting a compound of the formula (V):

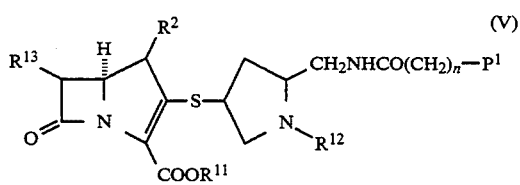

wherein $R^2$ is as hereinbefore defined; $R^{13}$ is a group $R^1$ or 1-(protected hydroxy)ethyl; $R^{11}$ is hydrogen or a carboxy protecting group; $R^{12}$ is hydrogen or an amino protecting group; n is as hereinbefore defined and $P^1$ is an optionally protected group P; with the proviso that there is at least one protecting group: and thereafter if necessary:

(i) forming a pharmaceutically acceptable salt, (ii) esterifying to form an in vivo hydrolysable ester.

Protecting groups may in general be chosen from any of the groups described in the literature or known to the skilled chemist as appropriate for the protection of the group in question, and may be introduced by conventional methods.

The compounds of the formula (V) are novel and form another aspect of the invention.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1-20 carbon atoms).

Examples of carboxy protecting groups include straight or branched chain (1-12C)alkyl groups (eg isopropyl, t-butyl); lower alkoxy lower alkyl groups (eg methoxymethyl, ethoxymethyl, isobutoxymethyl); lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg p-methoxybenzyl, o-nitrobenzyl, p-nitrobenzyl, benzhydryl and phthalidyl); tri(lower alkyl)silyl groups (eg trimethylsilyl and t-butyldimethylsilyl); diaryl(loweralkyl)silyl groups (eg. t-butyldiphenylsilyl); tri(lower alkyl)silyl lower alkyl groups (eg trimethylsilylethyl); and (2–6C)alkenyl groups (eg allyl and vinylethyl).

Methods particularly appropriate for the removal of carboxyl protecting groups, include for example, acid-, base-, metal- or enzymically-catalysed hydrolysis for groups such as p-nitrobenzyloxycarbonyl, hydrogenation and for groups such as o-nitrobenzyl, photolytically.

Examples of hydroxy protecting groups include lower alkenyl groups (eg allyl); lower alkanoyl groups (eg acetyl); lower alkoxycarbonyl groups (eg t-butoxycarbonyl); lower alkenyloxycarbonyl groups (eg allyloxycarbonyl); aryl lower alkoxycarbonyl groups (eg benzoyloxycarbonyl, p-methoxybenzyloxycarbonyl, o-nitrobenzyloxycarbonyl, p-nitrobenzyloxycarbonyl); tri lower alkylsilyl (eg trimethylsilyl, t-butyldimethylsilyl) and aryl lower alkyl (eg benzyl) groups. In addition two hydroxy groups substituted on adjacent carbon atoms, for example in the catechol moiety, may be protected in the form of a cyclic silyl ether.

Examples of amino protecting groups include formyl, aralkyl groups (eg benzyl and substituted benzyl, eg p-methoxybenzyl, nitrobenzyl and 2,4-dimethoxybenzyl, and triphenylmethyl); di-p-anisylmethyl and furylmethyl groups; lower alkoxycarbonyl (eg t-butoxycarbonyl); lower alkenyloxycarbonyl (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl); trialkylsilyl (eg trimethylsilyl and t-butyldimethylsilyl); alkylidene (eg methylidene); benzylidene and substituted benzylidene groups; and the phthalimido group.

Methods appropriate for the removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

In another aspect of the present invention the compounds of the formula (I) and the formula (V) may be prepared by a) reacting compounds of the formulae (VI) and (VII):

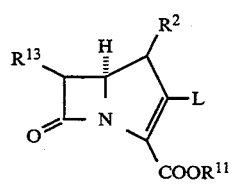

(VI)

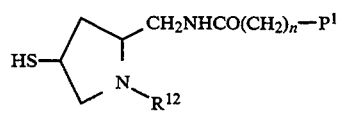

(VII)

wherein $P^1$, n, $R^2$, $R^{11}$, $R^{12}$ and $R^{13}$ are as hereinbefore defined and L is a leaving group, or (b) cyclising a compound of the formula (VIII):

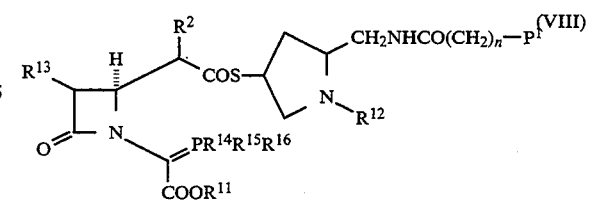

(VIII)

wherein $P^1$, n, $R^2$, $R^{11}$, $R_{12}$ and $R^{13}$ are as hereinbefore defined and $R^{14}$, $R^{15}$ and $R^{16}$ are independently selected from $C_{1-6}$alkoxy, aryloxy, di-$C_{1-6}$alkylamino and diarylamino or any two of $R^{14}$–$R^{16}$ represent o-phenylenedioxy; wherein any functional group is optionally protected and therein after if necessary:

(i) removing any protecting groups;
(ii) forming a pharmaceutically acceptable salt;
(iii) esterifying to form an in vivo hydrolysable ester.

Suitably in the compound of the formula (VI) L is the reactive ester of a hydroxy group such as a sulphonate (for example $C_{1-6}$alkanesulphonyloxy, trifluoromethanesulphonyloxy, benzenesulphonyloxy, toluenesulphonyloxy), a phosphoric ester (for example a diarylphosphoric ester such as diphenylphosphoric ester) or L is a halide (for example chloride). In an alternative L is a sulphoxide for example —SOCH=CH—NHCOCH$_3$ which may be readily displaced. Preferably L is diphenylphosphoric ester (—OP(O)(OPh)$_2$).

Compounds of the formula (VI) and their preparation are well known in the carbapenem literature, for example see EP-A-126587, EP-A-160391, EP-A-243686 and EP-A-343499.

The reaction between the compounds of the formulae (VI) and (VII) is typically performed in the presence of a base such as an organic amine for example di-isopropylethylamine or an inorganic base for example an alkali metal carbonate such as potassium carbonate. The reaction is conveniently performed at a temperature between −25° C. and ambient, suitably at about 0° C. The reaction is generally performed in an organic solvent such as acetonitrile or dimethylformamide. The reaction is generally performed in a manner similar to that described in the literature for similar reactions.

The compounds of the formula (VII) are novel and form another aspect of the present invention.

The compounds of the formula (VII) may be prepared by the deprotection of a compound of the formula (IX):

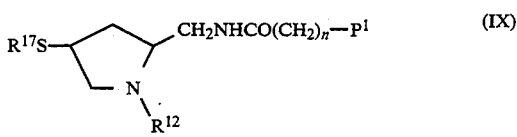

(IX)

wherein $P^1$, and n and $R^{12}$ are as hereinbefore defined and $R^{17}$ is a protecting group, for example $C_{1-6}$alkanoyl or $C_{1-6}$alkoxycarbonyl. Preferred values for $R^{17}$ are acetyl or t-butoxycarbonyl. The compounds of the formula (IX) can be converted to the compounds of the formula (VII) by standard methods of deprotection, for example acetyl groups can be removed by basic hydrolysis in aqueous alkanol, alkenol for example allyl alcohol or tetrahydrofuran.

The compounds of the formula (IX) are novel and form another aspect of the present invention.

The compounds of the formula (IX) may be prepared by the reaction of a compound of the formula (X) with a compound of the formula (XI) or activated derivative thereof, which may be formed in situ:

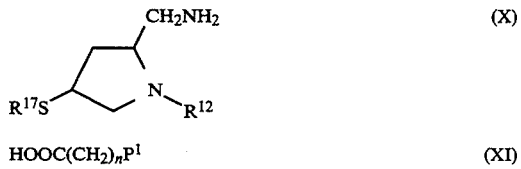

$$HOOC(CH_2)_nP^1 \quad\quad (XI)$$

wherein $P^1$, $n$, $R^{12}$ and $R^{17}$ and are as hereinbefore defined. Activated derivatives of the compound of the formula (XI) include activated esters, anhydrides such as 1H-benzol[1,2,3]triazol-1-yl, pentafluorophenyl and 2,4,5-trichlorophenyl esters of the benzimidazol-2-yl ester of the thiocarboxylic acid corresponding to (XI) and acid chlorides. The reaction of the compounds of the formulae (X) and (XI) is performed under standard methods of acylating amines, for example in the presence of Vilsmeier reagent (thus forming the reactive derivative of (XI) in situ) at temperatures in the range of $-30°$ C. to $+25°$ C., preferably in the region $-20°$ C. to $+5°$ C., or in the presence of sulphonyl chloride at ambient temperature.

The compounds of the formulae (X) and (XI) are prepared by standard methods known to the skilled man such as the methods of the Examples hereinafter, or by methods analogous or similar thereto.

Suitably, in the compounds of the formula (VIII), $R^{14}$ $R^{15}$ and $R^{16}$ are independently selected from $C_{1-6}$alkoxy such as methoxy, ethoxy, isopropoxy, n-propoxy or n-butoxy; aryloxy such as optionally phenoxy; di-$_{1-6}$alkylamino such as dimethylamino or diethylamino; diarylamino such as diphenylamino or any two or $R^{14}-R^{16}$ represent o-phenylenedioxy. Preferably each of $R_{14}-R^{16}$ have the same value and are $C_{1-6}$alkoxy for example methoxy, ethoxy, isopropoxy or n-butoxy or are phenoxy.

The compounds of the formula (VIII) are cyclized under conventional conditions known in the art to form compounds of the formula (V). Typical conditions are heating in a substantially inert organic solvent such as toluene, xylene or ethyl acetate at temperatures in the region $60°-150°$ C. Typically the reaction is performed in an atmosphere of nitrogen and is carried out in the presence of a radical scavenger for example hydroquinone.

The compounds of the formula (VIII) may be formed and cyclized in situ. The compounds of the formula (VIII) may conveniently be prepared by reacting compounds of the formulae (XII) and (XIII):

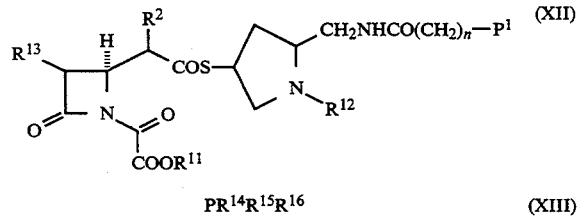

$$PR^{14}R^{15}R^{16} \quad\quad (XIII)$$

wherein $R^2$, $n$, $R^{11}-R^{16}$ and $P^1$ are as hereinbefore defined. Suitably the compound of the formula (XIII) is a phosphite or is the functional equivalent of such a compound.

The reaction between the compounds of the formulae (XII) and (XIII) is conveniently performed in an organic solvent such as toluene, xylene, ethyl acetate, chloroform, dichloromethane, acetonitrile or dimethylformamide. Typically the reaction is carried out at an elevated temperature for example $60-150°$ C.

The compounds of the formula (XII) may be prepared by a number of methods known in the art. For example the compounds of the formula (XII) may be prepared by the acylation of a compound of the formula (XIV):

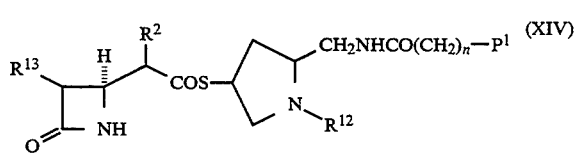

wherein $R^2$, $R^{12}$, $R^{13}$, $n$, and $P^1$ are as hereinbefore defined with a compound of the formula (XV):

$$Cl-CO-COOR^{11} \quad\quad (XV)$$

wherein $R^{11}$ is as hereinbefore defined.

The compounds of the formula (XIV) may be prepared by reacting compounds of the formulae (XVI) and (VII):

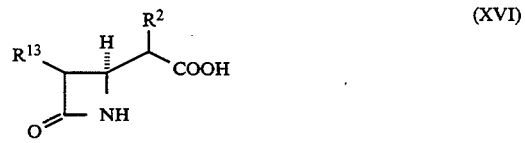

wherein $R^2$, and $R^{13}$ are as hereinbefore defined The compounds of the formula (XVI) are known in the art and may be reacted with the compounds of the formula (VII) under conventional acylation methods known in the art.

The following biological test methods, data and Examples serve to illustrate the present invention.

Antibacterial Activity

The pharmaceutically acceptable carbapenem compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. In particular the carbapenems of the present invention show good stability to beta-lactamases and have particularly high activity in vitro against strains of *Pseudomonas aeruginosa* and other Gram-negative aerobic bacteria.

The antibacterial properties of the compounds of the invention may also be demonstrated in vivo in conventional tests.

Carbapenem compounds have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in vitro test system using Diagnostic Sensitivity Test agar medium. The antibacterial activity is described in terms of the minimum inhibitory concentration (M1C) determined by the agar-dilution technique with an inoculum size of $10^4$ CFU/spot.

| ORGANISM | MIC (μg/ml) EXAMPLE 3 |
|---|---|
| P. aeruginosa PU21 (101028) | 0.25 |
| Ent. cloacae P99⁻ (401054) | 0.03 |
| Serr. marcesens (421003) | 0.25 |
| Pr. morganii (433001) | 0.5 |
| E. coli DCO (341098) | 0.03 |
| St. aureus 147N (601052) | 0.125 |
| S. dublin (369001) | 0.06 |
| Strep. pyogenes (681018) | 0.008 |
| P. aeruginosa 18S (101024) | 0.125 |
| P. aeruginosa 18S IMIR (101148) | 0.125 |
| B. fragilis AMP R (542008) | 4 |

In the examples:
(a) NMR spectra were taken at 200 MHz or 400 MHz in DMSO-$d_6$/CD$_3$COOD unless otherwise stated;
(b) Allyloxy means the propen-1-yloxy group —OCH$_2$CH=CH$_2$;
(c) THF means tetrahydrofuran;
(d) DMF means dimethylformamide;
(e) Meldrum's acid is 2,2-dimethyl-1,3-dioxane-4,6-dione;
(f) Dimedone is 5,5-dimethyl-1,3-cyclohexanedione.

EXAMPLE 1

(5R,6S,8R,2'S,4'S)-2-(2-(3,4-Dihydroxybenzoylaminomethyl)pyrrolidin-4-ylthio)-6-(1-hydroxyethyl)carbapenem-3-carboxylic acid.

A solution of p-nitrobenzyl (5R,6S,8R,2'S,4'S)-2-(1-p-nitrobenzyloxycarbonyl-2-(3,4-diallyloxybenzoylaminomethyl)pyrrolidin-4-ylthio-6-(1-hydroxyethyl)carbapenem-3-carboxylate (0.5 mM) and dimedone (1.0 mM) in tetrahydrofuran (3 ml) was purged with argon. A solution of tetrakis(triphenylphosphine)palladium (0.05 mM) in tetrahydrofuran (0.2 ml) was added and the resultant mixture was stirred under argon for 1 hour.

4-Morpholinepropanesulphonic acid buffer (15 ml) was added, followed by 10% palladium on carbon (500 mg) and the mixture was hydrogenated at atmospheric pressure for 1 hour. The mixture was filtered, tetrahydrofuran removed by evaporation, and the filtrate was washed with ethyl acetate prior to medium pressure chromatography on HP20SS resin (gradient elution with aqueous acetonitrile). The desired fractions were collected, evaporated to remove acetonitrile and freeze dried to give the title compound (14%):

NMR 1.15(d,3H); 1.62(m,1H); 2.55(m,1H); 3.15(m,3H); 3.26(dd,1H); 3.5(m,2H); 3.58(m,1H); 3.75(m, 1H); 3.83(m,1H); 3.92(m,1H); 4.1(dt,1H); 6.78(d,1H); 7.2(dd,1H); 7.35(d,1H).

EXAMPLE 2

(5R,6S,8R,2'S, 4'S)-2-(2-(5-Bromo-3,4-dihydroxybenzoylaminomethyl)pyrrolidin-4-ylthio)-6-(1-hydroxyethyl)carbapenem-3-carboxylic acid.

To a solution of allyl (5R,6S,8R,2'S,4'S)-2-(1-allyloxycarbonyl-2-(3,4-diallyloxy-5-bromobenzylaminomethyl)pyrrolidin-4-ylthio)-6-(1-hydroxyethyl)carbapenem-3-carboxylate (0.25 mM) and Meldrum's acid (2.0 mM) in dimethylformamide (1.3 ml), under an argon atmosphere, was added a solution of tetrakis(triphenylphosphine)palladium (0.015 mM) in tetrahydrofuran (0.2 ml). The solution was stirred, under argon with protection from the light, for 75 minutes. Tetrahydrofuran (2.5 ml) was added slowly to precipitate the product. The resultant suspension was stirred for 10 minutes, the product was collected by filtration, washed with tetrahydrofuran and ether and dried to give the title product (80%):

NMR: 1.1(d,3H); 1.69(m,1H); 2.55(m,1H); 3.19(m,4H); 3.53(m,2H); 3.63(m, 1H); 3.7(m,1H); 3.89(m,1H); 3.92(m, 1H); 4.11(dt,1H); 7.3(d,1H); 7.5(d,1H).

EXAMPLES 3–8

By the general method of Example 2, the following reactions were performed:

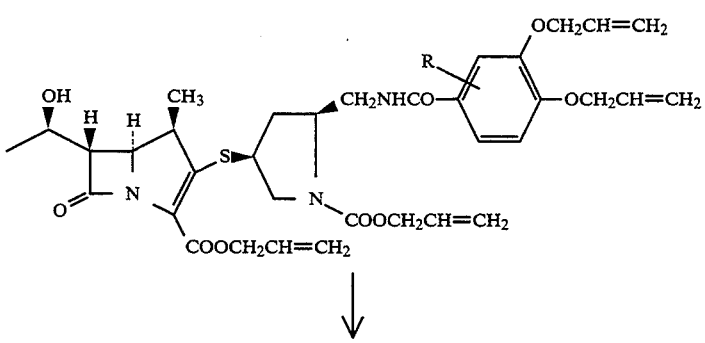

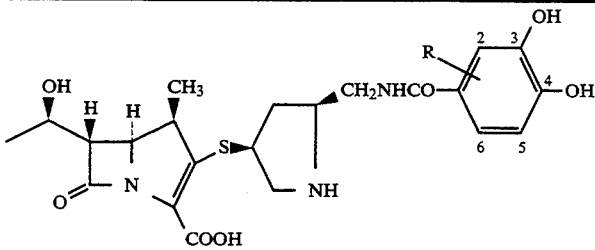

| Example | R | Yield | Solvent | Reaction Time |
|---|---|---|---|---|
| 3 | 5-CN | 88% | DMF (1.5 ml) | 20 min |
| 4 | 5-OH | 75% | DMF (0.5 ml) | 25 min |
| 5 | 6-COOH | 92% | DMF (1.8 ml) | 30 min |
| | (prepared from the corresponding 6-COOCH$_2$CH=CH$_2$ compound) | | | |
| 6 | 5-SO$_2$CH$_3$ | 92% | DMF (3.0 ml) | 30 min |
| 7 | 6-CONMe$_2$ | 80% | DMF (1.5 ml) | 36 min |
| 8 | 6-CN | 99% | DMF (2.0 ml) | 36 min |

Spectroscopic Data

EXAMPLE 3

NMR: 1.16(2d, 6H); 1.72(m,1H); 2.61(m, 1H); 3.25(m,2H); 3.39(m, 1H); 3.60(m, partially obscured); 3.72(m,2H); 3.98(m,2H); 4.20(d of d,1H); 7.58(d,1H); 7.63(d,1H): M/S +ve FAB (M+H)$^+$=503.

EXAMPLE 4

NMR: 1.12(d,6H); 1.7(m, 1H); 2.51(partially obscured); 3.20(m,2H); 3.32(m, 1H); 3.54(m,2H); 3.70(m,2H); 3.91(m,2H); 4.17(d of d,1H); 6.87(s,2H): M/S +ve FAB (M+H)$^+$=494.

EXAMPLE 5

NMR: 1.11(d,6H); 1.70(m,1H); 2.55(m, partially obscured); 3.22(m,2H); 3.35(m,1H); 3.49(m,2H); 3.72(m,2H); 3.88(m, 1H); 3.94(m,1H); 4.17(d of d,1H); 6.81(s,1H); 7.28(s,1H): M/S +ve FAB (M+H)$^+$=522.

EXAMPLE 6

NMR: 1.13(d,6H); 1.65(m, 1H); 2.56(m, partially obscured); 3.20(s,3H); 3.24(m, partially obscured); 3.34(m, 1H); 3.58(m,2H); 3.7(m,2H); 3.95(m,2H); 4.18(m, 1H); 7.60(s,1H); 7.78(s,1H): M/S +ve FAB (M+H)$^+$=556.

EXAMPLE 7

NMR: 1.1(d,6H); 1.68(m,1H); 2.6(m,1H); 3.2(m,2H); 3.35(m,1H); 3.58(m,2H); 3.7(m,2H); 3.95(m,2H); 4.17(dd,1H); 7.13(s,1H); 7.22(s,1H): M/S +ve FAB (M+H)$^+$=503.

EXAMPLE 8

NMR: 1.15(d,6H); 1.65(m, 1H); 2.53(m, partially obscured); 2.73(s,3H); 2.9(s,3H); 3.2(m,2H); 3.36(m, 1H); 3.5(m,2H); 3.68(m,2H); 3.92(m,2H); 4.18(m,1H); 6.6(s,1H); 7.15(s,1H): M/S +ve FAB (M+H)$^+$=549.

EXAMPLE 9

(1R,5S,6S,8R,2'S,4'S)-2-(2-(3,4-Dihydroxybenzoylaminomethyl)pyrrolidin-4-ylthio)-6-(1-hydroxyethyl)-1-methyl-carbapenem-3-carboxylic acid.

A solution of p-nitrobenzyl (1R,5S,6S,8R,2'S,4'S)-2-(1-p-nitrobenzyloxycarbonyl-2-(3,4-diallyloxybenzoylaminomethyl)pyrrolidin-4-ylthio)-6-(1-hydroxyethyl)-1-methyl-carbapenem-3-carboxylate (0.112 mM) and Meldrum's acid (0.325 mM) in tetrahydrofuran (2 ml) was purged with argon. To this was added a solution of tetrakis(triphenylphosphine) palladium (0.017 mM) in tetrahydrofuran (0.2 ml) and the solution, protected from light, was stirred at ambient temperature for 1 hour. Further tetrakis(triphenylphosphine) palladium (0/017 mM) in tetrahydrofuran (0.2 ml) was added and the solution stirred for a further hour. The solvent was removed under reduced pressure and the residue dissolved in ethyl acetate (2 ml) and water (2 ml). The resultant mixture was hydrogenated over 10% palladium on carbon (170 mg) at atmospheric pressure for 1 hour. The reaction mixture was diluted with ethyl acetate (5 ml) and water (5 ml), filtered, and the ethyl acetate layer was washed with water. The combined aqueous layers were washed with ethyl acetate and freeze dried to give the title compound (42%): NMR 1.18(2d,6H); 1.7(m,1H); 2.5(m,1H); 3.19(m,1H); 3.24(dd,1H); 3.35(m,1H); 3.59(m,2H); 3.65(m, 1H); 3.7(m,1H); 3.88(m,1H); 3.99(m,1H); 4.2(dd,1H); 6.82(d,1H); 7.25(dd,1H); 7.35(d,1H); M/S+ve FAB (M+H)$^+$=478.

EXAMPLE 10

(1R,5S,6S,8R,2'S,4'S)-2-(2-(4,5-Dihydroxypyridin-2-ylcarbonylaminomethyl)pyrrolidin-4-ylthio)-6-(1-hydroxyethyl)-1-methylcarbapenem-3-carboxylic acid.

To a stirred, partial solution of p-nitrobenzyl (1R,5 S,6S,8R,2'S,4'S)-2-(1-p-nitrobenzyloxycarbonyl-2-(4,5-diallyloxypyridin-2-ylcarbonylaminomethyl)pyrrolidin-4-ylthio)-6-(1-hydroxyethyl)-1-methyl-carbapenem-3-carboxylate (0.025 mM) and Meldrum's acid (0.6 mM) in tetrahydrofuran (4 ml), under argon, was added tetrakis(triphenylphosphine)palladium (0.025 mM) in tetrahydrofuran (0.5 ml). The mixture was stirred, protected from light, for 1 hour. Ethyl acetate (10 ml) and water (10 ml) were added and the mixture was hydrogenated over 10% palladium on carbon (300 mg) at atmospheric pressure for 90 minutes. The mixture was filtered and the aqueous phase washed with ethyl acetate and freeze dried to give the title compound (70%): NMR 1.10(m,6H); 1.62(m,1H); 2.52(m, partially obscured); 3.18(m,2H); 3.29(m,1H); 3.60(m,3H); 3.74(m, 1H); 3.85(m, 1H); 3.95(d of d,1H); 7.41(s,1H); 7.89(s,1H): M/S +ve FAB (M+H)hu +=479.

STARTING MATERIALS EXAMPLES 1–10

The starting materials for Examples 1–10 were prepared in the following general manner:

To a stirred solution of the appropriate 6-(1-hydroxyethyl)-2-oxo-carbapenam-3-carboxylic acid ester or 6-(1-hydroxyethyl)-1-methyl-2-oxocarbapenam-3-carboxylic acid ester (1 equivalent) and di-isopropylethylamine (1.1 equivalents) in acetonitrile at 0° C., under an argon atmosphere, was added dropwise diphenyl chlorophosphate (1.1 equivalents). The solution was stirred at ambient temperature for 30 minutes to form the corresponding 3-diphenylphosphoryloxycarbapenem.

The solution was cooled to 0° C. and di-isopropylethylamine (1.5 equivalents) and the appropriate sidechain pyrrolidin-4-yl mercaptan (1.3 equivalents) in acetonitrile were added. The resultant solution was stirred at 0° C. for 90 minutes, solvent was removed by evaporation and the desired product isolated by medium pressure chromatography on silica (eluting with propan-2-ol/dichloromethane) to give an amorphous foam.

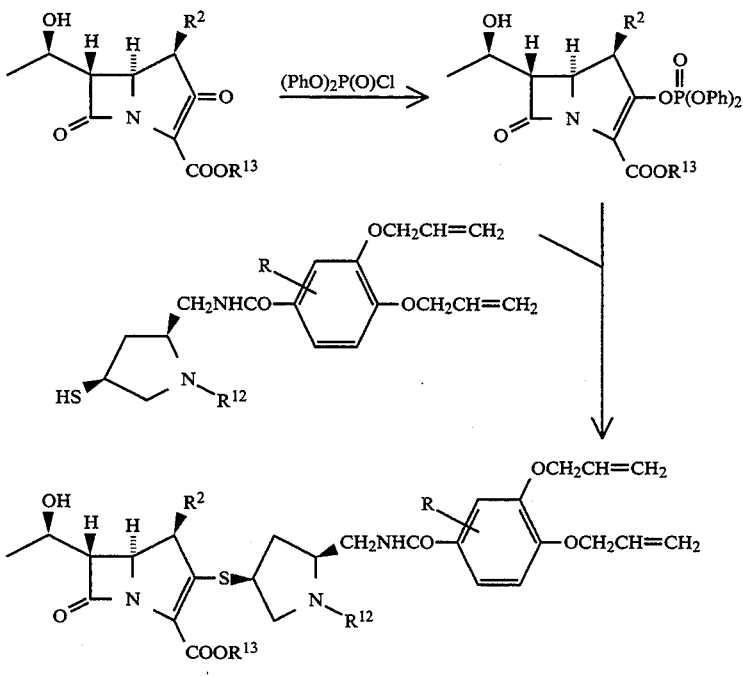

TABLE 2

| Preparation of starting material for Example | $R^2$ | R | $R^{13}$ | $R^{12}$ | Footnotes |
|---|---|---|---|---|---|
| 1 | H | H | PNB | $CO_2PNB$ | 1, 2, 3 |
| 2 | H | 5-Br | $CH_2CH=CH_2$ | $CO_2CH_2CH=CH_2$ | 1, 2, 4 |
| 3 | $CH_3$ | 5-CN | $CH_2CH=CH_2$ | $CO_2CH_2CH=CH_2$ | 5 |
| 4 | $CH_3$ | 5-OH | $CH_2CH=CH_2$ | $CO_2CH_2CH=CH_2$ | 5 |
| 5 | $CH_3$ | 6-COOCH$_2$—CH=CH$_2$ | $CH_2CH=CH_2$ | $CO_2CH_2CH=CH_2$ | 5 |
| 6 | $CH_3$ | 5-SO$_2$CH$_3$ | $CH_2CH=CH_2$ | $CO_2CH_2CH=CH_2$ | 5, 10 |
| 7 | $CH_3$ | 6-CN | $CH_2CH=CH_2$ | $CO_2CH_2CH=CH_2$ | 11, 12 |
| 8 | $CH_3$ | 6-CON(CH$_3$)$_2$ | $CH_2CH=CH_2$ | $CO_2CH_2CH=CH_2$ | 1, 13, 14 |
| 9 | $CH_3$ | H | PNB | $CO_2CO_2PNB$ | 2, 6, 7 |

TABLE 2-continued

| Preparation of starting material for Example | R² | R | R¹³ | R¹² | Footnotes |
|---|---|---|---|---|---|
| 10* | CH₃ | H | PNB | CO₂CO₂PNB | 8, 9 |

[PNB = p-nitrobenzyl]
*Preparation of the corresponding diallyloxypyridine

Footnotes to Table 2

1. Reaction time: 1 hour at 0° C. and 2–3 hours at ambient temperature.
2. Work-up by partitioning between dichloromethane and water, evaporating the organic phase and subjecting to chromatography.
3. Eluant: dichloromethane/tetrahydrofuran (3:1)
4. Eluant: ethyl acetate/hexane (9:1)
5. Eluant: ethyl acetate/dichloromethane (7:3)
6. Reaction time: 7 hours at 0° C.
7. Eluant: dichloromethane/tetrahydrofuran (5:1)
8. Eluant: ethyl acetate
9. Reaction time: 4 hours at 0° C. and 8 hours at ambient temperature.
10. Reaction time: 4 hours at 0° C.
11. Reaction time: 2.5 hours at 0° C.
12. Eluant: ethyl acetate/dichloromethane (1:1)
13. Eluant: isopropanol/dichloromethane (1:20)
14. Eluant: acetonitrile/ethyl acetate (gradient elution)

Spectroscopic data for Products of Table 2

1. NMR(DMSO-d₆)1.14(d, 3H);1.85(m, 1H);2.5(br s, partially obscured);3.30(br s, partially obscured);3.47(m, 2H);3.6(m, 1H);3.86(m, 1H);3.95(dd,1H);4.16(m, 3H);4.58(m, 4H);5.3(m, 8H); 6.05(m, 2H);7.0(d, 1H);7.42(m, 2H);7.68(2d, 4H);8.23(m, 4H);8.49(br s, 1H).
2. NMR (DMSO-d₆) 1.12(d, 3H);1.8(m, 1H);2.5(s, 1H);3.25(br s, 4H);3.45(m, 1H);3.6(m, 1H);3.8(m, 1H);4.05(m, 4H);4.6(m, 8H); 5.3(m, 8H);6.0(m, 4H);7.05(d, 1H);7.7(d, 1H);8.48(br t,1H):M/S+ve FAB(M+H)⁺ =746.
3. NMR 1.12(m, 6H);1.79(m, 1H);2.50(partially obscured); 3.11(m, 1H);3.20(d of d, 1H);3.45(m, 2H);3.62(m, 1H);3.78(m, 1H);3.95(m, 1H);4.05(m, 2H);4.19(d of d, 1H);4.51(m, 3H);4.72(m, 5H);5.31(m, 8H);5.96(m, 4H);7.77(m, 2H);M/S +ve FAB(M+H)⁺ =707.
4. NMR 1.12(d, 6H);1.88(m, 1H);2.50(partially obscured);3.11(m, 1H);3.19(d of d, 1H);3.45(m, 2H);3.58(m, 1H);3.74(m, 1H);3.94(m, 1H);4.04(m, 2H);4.18(d of d, 1H);4.50(m, 10H);5.2(m, 10H);5.92(m, 5H);7.14(s, 2H):M/S +ve FAB(M+H)⁺ =738.
5. NMR 1.14(m, 6H);1.86(m, partially obscured);2.48(m, partially obscured);3.11(m, 1H);3.21(m, 1H);3.34(m, 1H);3.49(m, 1H); 3.62(m, 1H);3.76(m, 1H);3.95(m, 1H);4.02(m, 2H);4.21(d of d, 1H); 4.60(m, 8H);5.38(m, 8H);5.95(m, 4H);7.00(s, 1H):M/S +ve FAB(M+H)⁺ =766.
6. NMR:1.17(d, 6H);1.70(m, 1H);2.54(m, partially obscured);3.13(m, 1H);3.24(m, 1H);3.27(s, 3H);3.46(m, 2H);3.65(m, 1H);3.80(m, 1H);3.96(m, 1H);4.07(m, 2H);4.20(m, 1H);4.65(m, 8H);5.3(m, 8H);6.0(m, 4H);7.85(s, 1H);7.94(s, 1H):M/S +ve FAB(M+H)⁺ =760.
7. NMR:1.12(d, 6H);1.8(m, 1H);2.55(m, partially obscured);3.10(m, 1H);3.20(dd, 2H);4.52(m, 2H);4.68(m, 6H);5.16(m, 2H);5.25(m, 3H);5.39(m, 3H);5.87(m, 2H);6.03(m, 2H);7.32(broad s, 1H);7.4(s, 1H):M/S +ve FAB(M+H)⁺ =707.
8. NMR:1.14(d, 6H);1.76(m, 1H);3.13(m, 1H);3.21(m, 1H);3.42(m, 2H);3.57(m, 1H);3.75(m, 1H);3.96(m, 1H);4.04(m, 2H);4.19(m, 1H);4.58(m, 8H);5.27(m, 8H);5.94(m, 4H);6.79(s, 1H);7.23(s, 1H):M/S +ve FAB(M+H)⁺ =753.
9. NMR (at 50° C.) 1.15(2d, 6H);1.86(m, 1H);2.56(m, partially obscured);3.21(m, 1H);3.27(dd, 1H);3.5(m, 2H);3.62(dd, 1H);3.85(m, 1H);4.02(dd, 1H);4.11(m, 1H);4.23(dd, 1H);4.56(m, 4H);5.3(m, 8H);6.03(m, 2H);6.98(d, 1H);7.42(m, 2H);7.63(d, 2H);7.69(d, 2H);8.17(2d, 4H):M/S +ve FAB(M+H)⁺ =872.
10. NHR 1.15(m, 6H);1.80(m, 1H);2.52(m, partially obscured);3.07(m, partially obscured);3.22(m, partially obscured);3.52(m, 2H);3.62(m, 1H);3.82(m, 1H);3.99(m, 1H);4.14(m, 1H);4.2(br s, 1H);4.26(d of d, 1H);4.71(m, 4H);5.24(m, 5H);5.42(m, 3H);6.05(m, 2H);7.59(s, 1H);7.67(m, 4H);8.15(m, 5H):M/S +ve FAB(M+H)⁺ =873.

Esters of 6-(1-hydroxyethyl)-2-oxocarbapenem carboxylic acid and 6-(1-hydroxyethyl)-1-methyl-2-oxocarbapenam carboxylic acid are well known in the literature, see for example EP-A-126780 and EP-A-208889.

We prefer to prepare p-nitrobenzyl and allyl 6(1-hydroxyethyl)-1-methyl-2-oxocarbapenam carboxylates in situ from the corresponding 2-diazo-3-oxo-4-methyl-4-(3-(1-hydroxyethyl)-2-oxoazetidin-4-yl)-butanoate and rhodium octanoate (see for example EP-A-341557 and Tet Lett 1988, 29, 61)

PREPARATION OF SIDE CHAIN PYRROLIDIN-4-YL MERCAPTANS 1-p-Nitrobenzyloxycarbonyl-2-(3,4-diallyloxybenzoylaminomethyl)pyrrolidin-4-yl thiol.

This compound was prepared according to Scheme A:

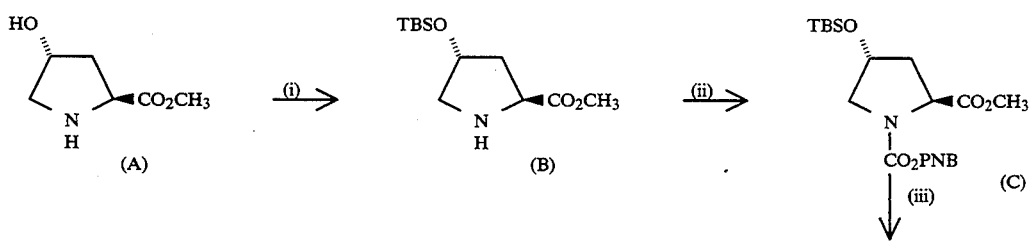

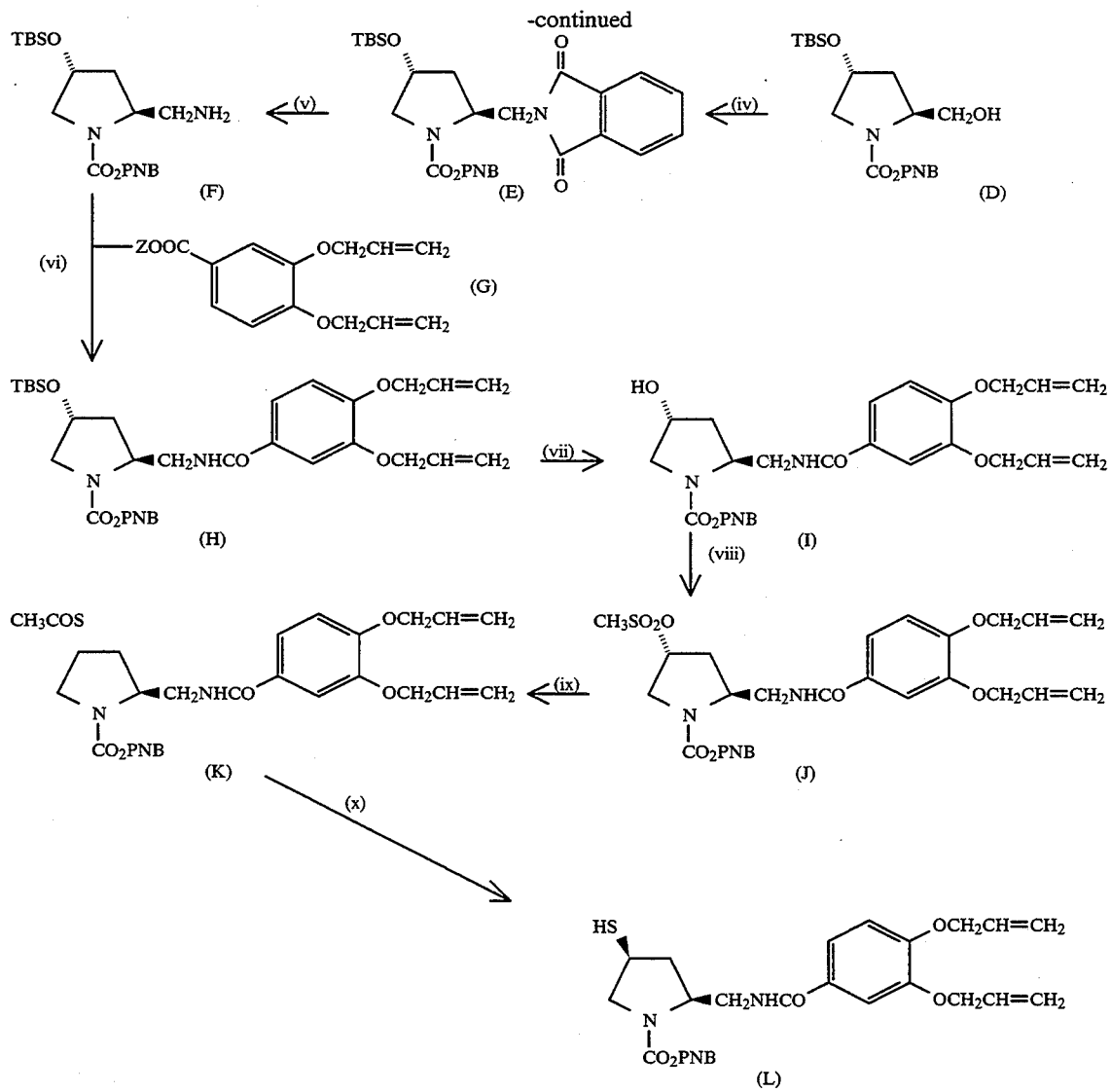

TBS = t-butyldimethyl silyl
PNB = p-nitrobenzyl
Z = H or 2,5-dioxopyrrolidin-1-yl (i) To a suspension of 4-hydroxyproline methyl ester hydrochloride (Rosen et al., Synthesis, 40, 1988) (60 mMol) in dichloromethane (50 ml) was added imidazole (240 mMol) and t-butyldimethylsilyl chloride (120 mMol). The mixture was stirred at ambient temperature for 16 hours, under argon, and partitioned between dichloromethane and water. The organic layer was washed ($H_2O$, 1N HCl, $H_2O$, $NaHCO_3$), dried and evaporated to give compound (B) (83%); NMR ($CDCl_3$) 0.0(s,6H); 0.82(s,9H); 1.95(m,2H); 2.82(m, 1H); 3.15(m, 1H); 3.68(s,3H); 4.00(br t,1H); 4.21(m,1H); 4.34(m,1H).

(ii) The product from (i) above (30 mMol) in THF (30 ml) was treated with triethylamine (30 mMol) and p-nitrobenzyl chloroformate (30 mMol) in THF (30 ml). The mixture was stirred for 4 hours at ambient temperature, diluted with ether and the organic phase washed ($H_2O$, 1N HCl, $H_2O$, $NaHCO_3$), dried and evaporated to give a residue. This was purified by flash column chromatography on silica (ethyl acetate/hexane 1:3) to give, as a colourless oil, compound (C) (82%): NMR 0.0(s,6H); 0.8(s,9H); 2.1(m,2H); 3.43(m, 1H); 3.62(m,4H); 3.44(m,2H); 5.15(m,2H); 7.4(t,2H); 8.25(d,2H): M/S [EI+] 439.

(iii) Compound (C) (18.4 mMol) in ether (120 ml) was treated with lithium borohydride (26.92 mMol). The mixture was stirred at ambient temperature for 2 hours, quenched by the dropwise addition of water and the aqueous layer extracted with ethyl acetate (50 ml) and dichloromethane (50 ml). The combined organic layers were dried and evaporated to give, after flash column chromatography (ether/hexane), compound (D): NMR ($CDCl_3$) 0.0(2s,6H); 0.8(s,9H); 1.6(m,2H); 1.95(m, 1H); 3.46(m,2H); 3.54(m,1H); 3.73(m, 1H); 4.12(m,1H); 4.31(m, 1H); 5.2(q,2H); 7.45(d,2H); 8.17(d,2H): M/S (CI+) 411.

(iv) To a solution of Compound (D) (26.2 mMol) in THF (30 ml), triphenylphosphine (39.3 mMol) and phthalimide (39.3 mMol), was added, dropwise, diethylazodicarboxylate (39.3 mMol). The mixture was stirred for 18 hours, at ambient temperature, evaporated and subjected to flash column chromatography (ethyl acetate/hexane 1:3) to give, as a pale yellow oil, compound (E): NMR (CDCl3) 0.02(s,6H); 0.84(s,9H); 1.98(m,2H); 3.49(m,2H); 3.84(m,2H); 4.43(m,2H); 5.19(m,2H); 7.43(d,1H); 7.53(d,1H); 7.7(m,2H); 7.8(m,2H); 8.17(dd,2H): M/S FAB (M+H)+=540.

(v) To a solution of Compound (E) (3.98 mMol) in ethanol (30 ml) was added hydrazine hydrate (8 mMol). The mixture was stirred at reflux for 3 hours, allowed to stand overnight, filtered and the filtrate evaporated to give, after chromatography (CH2Cl2/CH3OH/NH3 in CH3OH 95:2.5:2.5), compound (F) as a yellow oil: NMR (CDCl3) 0.06(s,6H); 0.85(s,9H); 1.33(br s,2H); 1.98(m,2H); 2.88(br s,2H); 3.46(m,2H); 4.02(m, 1H); 4.39(m,1H); 5.23(m,2H); 7.5(d,2H); 8.2(d,2H): M/S (CI+)=410.

(vi) Compound (F) (6.47 mMol) was dissolved in dichloromethane (5ml) containing triethylamine (6.58 mMol). A solution of 3,4-diallyloxybenzoylchloride (6.5 mMol) in dichloromethane (5 ml) was added. The mixture was stirred at ambient temperature for 18 hours, poured into dichloromethane/water and the organic layer was separated, washed (1N HCl, H2O, NaHCO3, H2O), dried and evaporated. The residue was purified by column chromatography (ethyl acetate/hexane 3:7) to give compound (H) as a yellow oil: NMR (CDCl3) 0.03(2d, 6H); 0.82(s,9H); 1.83(m, 1H); 2.1(m, 1H); 3.33(m,2H); 3.62(m,2H); 4.26(m,1H); 4.37(m,1H); 4.62(m,4H); 5.34(m,6H) 6.02(m,2H); 6.84(d,1H); 7.32(m,1H); 7.48(m,3H); 8.01(br s,1H); 8.16(d,2H): M/S +ve FAB (M+H)+=626.

(vii) To a solution of compound (H) (2.76 mMol) in THF (20 ml) was added 1N HCl (3 mMol). The mixture was heated at reflux for 3 hours and diluted with dichloromethane (40 ml) and saturated aqueous sodium bicarbonate (40 ml). The organic layer was separated, dried and purified by column chromatography (methanol/dichloromethane 5:95) to give compound (I): NMR (CDCl3) 1.96(m,1H); 2.21(m,1H); 3.45(m,2H); 3.76(m,2H); 4.32(m,1H); 4.5(m,1H); 4.63(m,4H); 5.35(m,6H; 6.09(m,2H); 6.87(d,1H); 7.31(m,1H); 7.47(m,3H); 8.03(br s,1H); 8.17(d,2H): M/S +ve FAB (M+H)+=512.

(viii) To a solution of compound (I) (0.93 mMol) and triethylamine (2.06 mMol) in THF (5.17 ml) was added, dropwise, methanesulphonyl chloride (2.06 mMol) in THF (1.4 ml). The mixture was stirred at ambient temperature for 1 hour and evaporated. The residue was taken up in dichloromethane (20 ml) and water (20 ml), the organic layer was dried and evaporated to give compound (J): NMR (CDCl3) 2.1(m,1H); 2.54(m, 1H); 3.06(s,3H); 3.4(m, 1H); 3.65(dd,1H); 3.85(m, 1H); 4.16(br d,1H); 4.32(m,1H); 4.64(br d,4H); 5.34(m,6H); 6.08(m,2H); 6.87(d,1H); 7.3(dd,1H); 7.49(m,3H); 7.8(br s,1H); 8.21(d,2H): M/S +ve FAB (M+H)+=590.

(ix) Thiolacetic acid (10.6 mMol) in DMF (7 ml) was added to sodium hydride (10.34 mMol; washed free of oil) in DMF (7 ml). After 45 minutes, sodium iodide (3.6 mMol) and compound (J) (3.41 mMol) were added in DMF (6.5 ml). The mixture was heated at 70°-80° C. for 12 hours, diluted with water and extracted into ethyl acetate (3×30 ml). The organic extracts were combined, washed (sodium sulphite, water, brine), dried and evaporated to give, after flash column chromatography (ethyl acetate/hexane 1:1), compound (K) as an off-white solid: NMR (CDCl3) 1.8(m, 1H); 2.35(s,3H); 2.65(m,1H); 3.3(m, 1H); 3.5(m, 1H); 3.77(m, 1H); 3.9(m, 1H); 4.2(m,2H); 4.64(m,4H); 5.36(m,6H); 6.1(m,2H); 6.85(d,1H); 7.31(dd,1H); 7.49(m,3H); 7.95(br s,1H); 8.21(d,2H): M/S FAB (M+H)+=570.

(x) Compound (K) was dissolved in methanol and the solution flushed with argon. 1N Sodium hydroxide (1.1-1.5 equivalents) was added and the mixture was stirred at ambient temperature for 60 minutes. 2N Hydrochloric acid (1.1-1.5 equivalents) was added, methanol removed by evaporation and the residue partitioned between ethyl acetate and water. The organic layer was washed with brine, dried (MgSO4) and evaporated to give 1-p-nitrobenzyloxycarbonyl-2-(3,4-diallyloxybenzoylaminomethyl)pyrrolidin-4-yl thiol (compound (L)): NMR: (CDCl3) 1.67(s,1H); 1.93(m, 1H); 2.56(m,1H); 3.41(m,2H); 3.6(m,1H); 3.82(m, 1H); 4.04(m,1H)4.2(m, 1H); 4.53(m,4H); 5.35(m,6H); 6.08(m,2H); 6.87(d,1H); 7.03(m, partially obscured); 7.49(m,3H); 7.83(br s,1H); 8.2(d,2H)

1-Allyloxycarbonyl-2-(3,4-diallyloxy-5-bromobenzoylaminomethyl)pyrrolidin-4-ylthiol In a method similar to (i)-(x) above, the corresponding 1-allyloxycarbonyl-2-(3,4-diallyloxy-5-bromobenzoylaminomethyl)pyrrolidin-4-ylthiol was prepared. The 4-acetylthio derivative (corresponding to compound (K)) had NMR: (CDCl3) 1.75(m,1H); 2.35(s,3H); 2.65(m,1H); 3.27(m,1H); 3.43(m,1H); 3.76(m,1H); 3.91(m, 1H); 4.15(m,2H); 4.62(m,6H); 5.34(m,6H); 6.0(m,3H); 7.41(d,1H); 7.63(br s,1H); 8.36(br s,1H).

1-Allyoxycarbonyl-2-(3,4-diallyloxy-5-methanesulphonylbenzoylaminomethyl)pyrrolidin-4-ylthiol In a method similar to (i)-(x) above, the corresponding 1-allyloxycarbonyl-2-(3,4-diallyloxy-5-methanesulphonylbenzoylaminomethyl)pyrrolidin-4-ylthiol was prepared. The 4-acetylthio derivative (corresponding to compound (K) had NMR: (DMSO-d6) 1.44(s, 9H); 1.77(m, 1H); 2.42(m, partially obscured); 3.27(s, 3H); 3.56(m, 2H); 3.70(m, 2H); 4.05(m, 2H); 4.53(m, 2H); 4.73(m, 4H); 5.34(m, 6H); 6.11(m, 3H); 7.84(d, 1H); 7.92(d, 1H); 8.76(br. m, 1H).

The thiol (L) had NMR: 1.17(d, 6H); 1.72(m, 1H); 2.54(m, partially obscured); 3.13(m, 1H); 3.24(m, 1H); 3.27(s, 3H); 3.46(m, 2H); 3.65(m, 1H); 3.80(m, 1H); 3.96(m, 1H); 4.07(m, 2H); 4.20(m, 1H); 4.65(m, 8H); 5.3(m, 8H); 6.0(m, 4H); 7.85(s, 1H); 7.94(s, 1H).

1-p-Nitrobenzyloxycarbonyl-2-(4,5-diallyloxypyridin-2-ylcarbonylaminomethyl)pyrrolidin-4-ylthiol (i) Comenamic acid (0.2M) and silver carbonate (0.33M) in toluene (750 ml), protected from light, were stirred under reflux (Dean Stark apparatus) for 90 minutes. The mixture was cooled, allyl bromide (0.6M) added and heating at reflux continued for a further hour. The mixture was filtered whilst hot, washing well with toluene, and evaporated to give, after medium pressure chromatography (ethyl acetate/hexane 35:65), as a waxy solid, allyl 4,5-diallyloxypyridin-2-ylcarboxylate: NMR (CDCl3) 4.73(m,4H); 4.87(d of t,2H); 5.38(m,6H); 6.06(m,3H)7.69(s,1H); 8.25(s,1H): M/S CI (M+H)+=275.

(ii) The product from (i) above (50 mM) was heated under reflux with 1N aqueous potassium hydroxide (75 ml) for 15 minutes. The solution was treated with charcoal, filtered whilst hot, cooled and acidified with glacial acetic acid (0.1M). The product crystallised, was collected and recrystallised from ethyl acetate to give 4,5-diallyloxypyridin-2-yl carboxylic acid: NMR (DMSO-d6) 4.83(m,4H); 5.87(m,4H); 6.06(m,2H); 7.75(s,1H); 8.31(s,1H): M/S CI (M+H)+=236.

(iii) To the product from (ii) above (5 mM) in dichloromethane (15 ml) at 0° C., was added di-isopropylethylamine (5.5 mM) followed by the slow addition of isobutyl chloroformate (5.0 mM) in dichloromethane (5 ml). The solution was stirred at 0° C. for 30 minutes and 1-p-nitrobenzyloxycarbonyl-2-aminomethyl-4-t-butyldimethylsilyloxypyrrolidine (compound (F)) (4.9 mM) in dichloromethane (10 ml) was slowly added. The solution was allowed to warm to ambient temperature, stirred for 1 hour, washed (2N HCl, H$_2$O, 2N NaOH brine), dried and evaporated to give, after medium pressure chromatography (ethyl acetate/hexane 35:65), 1-p-nitrobenzyloxycarbonyl-2-(4,5-diallyloxypyridin-2-ylcarbonylaminomethyl)-4-t-butyldimethylsilyl oxypyrrolidine as a gum: NMR (CDCl$_3$) 0.01(d,6H); 0.82(s,9H); 1.94(m,2H); 3.6(m,4H); 4.23(m,1H); 4.38(m,1H); 4.70(m,4H);5.34(m,6H); 6.05(m,2H); 7.52(d,2H); 7.71(s,1H); 8.07(s,1H); 8.18(d,2H); 8.42(br s,1H): M/S +ve FAB (M+H)$^+$=627.

(iv) The compound from (iii) above was hydrolysed with 1N HCl [see section (vii) above] to give the corresponding alcohol: NMR (CDCl$_3$) 2.09(m,2H); 3.66(m,4H); 4.28(m, 1H); 4.47(m,1H); 4.70(m,4H); 5.37(m,6H); 6.05(m,2H); 7.53(d,2H); 7.71(s,1H); 8.07(s,1H); 8.20(d,2H); 8.38 (br s,1H): M/S +ve FAB (M+H)$^+$=513.

(v) The compound from (iv) above was acylated with methanesulphonyl chloride [see section (viii) above] to give the corresponding mesylate which was used without further purification to form the corresponding 4-acetylthio compound [see section (ix) above]: NMR (CDCl$_3$/CD$_3$COOD) 1.85(m, 1H); 2.32(s,3H); 2.58(m, 1H); 3.25(m,1H); 3.76(m,2H); 3.91(m, 1H); 4.19(m,2H); 4.72(m,4H); 5.36(m,6H); 6.08(m,2H); 7.53(d,2H); 7.77(s,1H); 8.02(br d,1H); 8.18(d,2H): M/S +ve FAB (M+H)$^+$=571.

(vi) The 4-acetylthio compound was hydrolysed [see section (x) above] to give the corresponding thiol as a gum which was used without further purification.
1-Allyloxycarbonyl-2-(3,4-diallyloxy-5-cyanobenzoylaminomethyl)pyrrolidin-4-ylthiol (i) To a stirred solution of 3,4-diallyloxy-5-cyanobenzoic acid (1.6 mMol) in dichloromethane was added oxalyl chloride (3.2 mMol) and DMF (10 μl). Further DMF (10 μl) was added after 30 minutes, stirring was continued for a further 30 minutes, the solvent was removed by evaporation and the residue taken up into toluene. This was filtered and the filtrate evaporated to give the acid chloride. This was dissolved in THF (2 ml) and added slowly to 1-allyloxycarbonyl-2-aminomethyl-4-t-butoxycarbonylthiopyrrolidine* (1.5 mMol) and di-isopropylethylamine (2.25 mMol) in THF (8 ml). The resultant mixture was stirred at ambient temperature for 30 minutes, diluted with ethyl acetate, washed (2N HCl, H$_2$O, NaHCO$_3$, brine, dried and evaporated to give, after medium pressure chromatography (ethyl acetate/hexane 3:7), 1-allyloxycarbonyl-2-(3,4-diallyloxy-5-cyanobenzoylaminomethyl)-4-t-butoxycarbonylthiopyrrolidine (87%): NMR (CDCl$_3$) 1.50(s,9H); 1.76(m,1H); 2.68(m,1H); 3.38(m,2H); 3.76(m,2H); 4.17(m,2H); 4.65(m,4H); 4.81(m,2H); 5.34(m,6H); 6.01(m,3H); 7.60(br s,1H); 7.69(d,1H): M/S +ve FAB (M+H)$^+$=558.
* [For the preparation of this, see below]

(ii) To the compound from (i) above (1.1 mMol) in glacial acetic acid (2 ml) was added 45% HBr in acetic acid. The mixture was stirred for 10 minutes, extracted into ethyl acetate, washed (NaHCO$_3$, H$_2$O, 2N HCl brine), dried and evaporated to give the thiol as a gum. This was used without further purification.

1-Allyloxycarbonyl-2-(3,4,5-diallyloxybenzoylaminomethyl)pyrrolidin-4-ylthiol

In a method similar to (i) and (ii) above [preparation of corresponding 5-cyano compound], the corresponding 5-allyloxy compound was prepared. The 4-t-butoxycarbonylthio compound had NMR: (CDCl$_3$): 1.51(s,9H); 1.75(m,1H); 2.64(m, 1H); 3.35(m,2H); 3.73(m,2H); 4.17(m,2H); 4.62(m,8H); 5.31(m,8H); 6.01(m,4H); 7.13(s,2H).

The 4-t-butoxycarbonylthio compound was treated with saturated HCl/acetic acid at 100° C. for 15 minutes to give, after work-up as above, the thiol as an oil. This was used without further purification.
1-Allyl-2-(3,4-diallyloxy-6-allyloxycarbonylbenzoylaminomethyl)pyrrolidin-4-ylthiol 4,5-Diallyloxyphthalic anhydride* (4 mMol) in allyl alcohol (10 ml) was heated under reflux for 18 hours. The solution was evaporated and purified by medium pressure chromatography (eluting with methanol/dichloromethane 1:9). 3,4-Diallyloxy-6-allyloxycarbonylbenzoic acid (91%) was obtained by crystallisation and trituration under ether: NMR (DMSO-d$_6$) 4.59(m,6H); 5.30(m,6H); 6.01(m,3H); 6.89(s,1H); 7.38(s,1H).

[* 4,5-Diallyloxyphthalic anhydride was prepared by alkylating dimethyl 4,5-dihydroxyphthalate (Reetz et al, Ber, 112, 2209, 1979) with allylbromide/K$_2$CO$_3$ in acetone: hydrolysing the product in NaOH/methanol to give the diacid and heating with acetic anhydride].

This was treated as in (i) and (ii) [preparation of corresponding 5-cyano compound] to give the thiol as a gum: NMR (DMSO-d$_6$) 1.75(m,1H); 2.44(m, partially obscured); 2.88(d, 1H); 3.03(m,1H); 3.29(m, partially obscured); 3.63(m,1H); 3.93(m,2H); 4.52(m,2H); 4.66(m,6H); 5.3(m,8H); 6.00(m,4H); 7.05(s,1H); 7.32(s,1H); 8.32(m,1H).
1-Allyloxycarbonyl-2-(3,4-diallyloxy-6-cyanobenzoylaminomethyl) pyrrolidin-4-ylthiol.

(i) A solution of 1-allyloxycarbonyl-2-aminomethyl-4-t-butoxycarbonylthiopyrrolidine (10 mmol) in acetic acid (25 ml), was saturated with hydrogen chloride and heated on a steam bath for 5 minutes. The solution was filtered and the filtrate evaporated. The residue was taken up in 2.5N aqueous solution of sodium hydroxide (25 ml) and ethanol (10 ml). A solution of potassium hexacyanoferrate (11 mmols) in water (20 ml) was added portion wise until a yellow colour persisted. The reaction was stirred at room temperature for 1 hour. The reaction mixture was partitioned between water and dichloromethane. The organic layer was washed with water, a saturated aqueous solution of sodium chloride and dried (MgSO$_4$). The solvent was removed by evaporation to give diallyl 4,4'-dithiodi[2-(aminomethyl)pyrrolidin-1-carboxylate] as a brown oil. NMR (DMSO-d$_6$): 1.88(m,1H); 2.34(m,2H); 2.87(m, partially obscured); 3.20(m,1H); 3.55(m,1H); 3.76(m, 1H); 3.90(m,1H); 4.5(m,1H); 5.2(m,2H); 5.94(m,1H): M/S CI (M+H)$^+$=431.

(ii) To a stirred solution of 3,4-diallyloxy-6-cyanobenzoic acid (3.0 mmol) in dichloromethane (10 ml) was added oxalyl chloride (6.0 mmol) and DMF (1 drop). After stirring for 30 minutes, additional DMF (1 drop) was added. The mixture was stirred for 30 minutes and the solvent evaporated. The residue was dissolved in toluene, filtered and evaporated. The residue was dissolved in dichloromethane (5 ml) and added dropwise to a solution of diallyl 4,4'-dithiodi[2-(aminomethyl)-pyrrolidin-1-carboxylate] (1.5 mmol) and diisopropylethylamine (3.3 mmol) in dichloromethane (10 ml). After two hours the precipitate was filtered off. The organic solution was washed with a 2N aqueous solution of hydrochloric acid, water and a saturated aqueous solution of sodium hydrogen carbonate and dried (MgSO$_4$). The solvent was evaporated to give diallyl 4,4'-dithiodi[2-(4,5-diallyloxy-2-cyanobenzoylaminomethyl)pyrrolidin-1-carboxylate] NMR (DMSO-d$_6$): 1.88(m,1H); 2.40(m,1H); 3.25(m,1H); 3.57(m,3H); 4.00(m,2H); 4.52(m,2H); 4.68(m,4H); 5.3(m,6H); 6.0(m,3H); 7.37(s,1H); 7.43(s,1H); 8.6(broad s,1H): M/S +ve FAB (M+H)$^+$=912.

(iii) To a stirred partial solution of the dithio compound prepared above (0.5 mmol) in cyanomethane (10 ml) was added water (5.0 mmol) followed by tri-n-butylphosphine. The reaction was heated at reflux for 10 minutes. The solution was dried over 4A molecular sieves and the solvent evaporated. the title compound thus obtained was used without further purification or characterisation.

1-Allyloxycarbonyl-2-(3,4-diallyloxy-6-di[N-methyl]-carbamoyl benzoylaminomethyl)pyrrolidin-4-ylthiol (i) To a stirred solution of 4,5-di(allyloxy)-2-(2,5-dioxopyrrolidin-1-yloxycarbonyl)-1-N,N-dimethylbenzamide (3.0 mmol) in dichloromethane (15 ml) was added a solution of the dithio compound from (i) above (1.5 mmol) in dichloromethane (10 ml). The reaction was stirred at ambient temperature for 2 hours, washed with a 2N aqueous solution of hydrochloric acid, then brine and dried (MgSO$_4$). The solvent was evaporated and the product purified by medium pressure liquid chromatography eluting with methanol/dichloromethane to give diallyl 4,4'-dithiodi[2-(4,5-diallyloxy-2-di(N-methyl)carbamoylbenzoylaminomethyl)pyrrolidin-1-carboxylate] as a foam. NMR (DMSO-d$_6$) 1.8(m, 1H); 2.38(m, 1H); 2.7(s, 3H); 2.9(s, 3H); 3.4(m, partially obscured); 3.55(m, 2H); 3.88(m, 2H); 4.58(m, 6H); 5.32(m, 6H); 6.03(m, 3H); 6.80(s, 1H); 7.28(s, 1H); 8.30(br, s, 1H): m/s +ve FAB (M+H)$^+$=1005.

(ii) To a stirred partial solution of the dithio compound from (i) (0.5 mmol) in cyanomethane (10 ml), was added water (5.0 mmol) followed by tri-n-butylphosphine (0.75 mmol). The mixture was heated at reflux for 10 minutes. The solution was dried over 4A molecular sieves and the solvent evaporated. The 1-allyloxycarbonyl-2-(3,4-diallyloxy-6-di{N-methyl]carbamoylbenzoylaminomethyl)pyrrolidn-4ylthiol thus prepared was used without further purification or characterisation.

Preparation of 1-allyloxycarbonyl-2-aminomethyl-4-t-butoxycarbonylthiopyrrolidine a) To a solution of 4-hydroxyproline methyl ester hydrochloride (Rosen et al, Synthesis, 40, 1988) (60.4 mMol) in water (10 ml) and THF (20 ml), at 0° C., was added dropwise allyl chloroformate (70 mMol) in THF (20 ml). The solution was maintained at a slightly basic pH by the simultaneous addition of 4N sodium hydroxide (144 mMol). The mixture was stirred at 0° for 1 hour. The aqueous layer was separated and washed, twice, with dichloromethane (25 ml). The organic layers were combined, dried and evaporated to give N-allyloxycarbonyl hydroxyproline methyl ester as a pale yellow oil (86%): NMR (CDCl$_3$) 2.2(m, 3H); 3.58(m, 2H); 3.73(2d, 3H); 4.54(m, 4H); 5.25(m, 2H); 5.9(m, 1H) M/S CI (M+H)$^+$=230.

b) The product from a) above (52.5 mMol) in THF (60 ml), at 0° C., was treated with triphenylphosphine (55 mMol) and diethylazodicarboxylate (61 mMol). The mixture was stirred at 0° C. for 30 minutes. Thiolacetic acid (55mMol) was added, the mixture allowed to warm to ambient and left to stand for 18 hours. The solvent was removed by evaporation and the residue purified by flash column chromatography (ethyl acetate: hexane 1:4 to 1:2) to give 1-allyloxycarbonyl-2-methoxycarbonyl-4-acetylthiopyrrolidine as a yellow oil (53%): NMR (CDCl$_3$) 2.0(m, 1H); 2.3(s, 3H); 2.75(m, 1H); 3.38(dd, 1H); 3.73(s, 3H); 4.05(m, 2H); 4.4(dd, 1H); 4.59(m, 2H); 5.25(m, 2H); 5.59(m, 1H): M/S CI (M+H)$^+$=288.

c) The product from b) above (16.3 mMol) in ethanol (8 ml) was stirred with methylamine in ethanol (35% solution; 18mMol) for 2 hours at room temperature. The mixture was evaporated and the residue dissolved in ethyl acetate (40 ml). This was washed with 1N HCl (20 ml) and water (2×20 ml), dried and evaporated to give the thiol. This was dissolved in THF (8 ml), cooled to 0° C., and treated with dimethylaminopyridine (0.35mMol), triethylamine (17 mMol) and, dropwise, di-t-butoxycarbonyl ether (17 mMol) in THF (8 ml). The mixture was allowed to warm to room temperature, stirred for 18 hours and evaporated. The residue was purified by flash chromatography (ethyl acetate/hexane 1:4) to give 1-allyloxycarbonyl-2-methyloxycarbonyl-4-t-butoxycarbonylthiopyrrolidine as a colourless oil (74%): NMR (CDCl$_3$) 1.48(s, 9H); 2.04(m, 1H); 2.74(m, 1H); 3.46(dd, 1H); 3.73(m, 4H); 4.1(m, 1H); 4.4(m, 1H); 4.6(m, 2H); 5.25(m, 2H); 5.9(m, 1H): M/S CI (M+H)$^+$=346.

d) The product from c) above (1.72 mMol) in anhydrous diethyl ether (60 ml) and lithium borohydride (16 mMol) was heated at reflux for 1 hour. The mixture was cooled, quenched with water (10 ml) added dropwise and extracted into dichloromethane (2×20 ml). The organic layers were dried, evaporated and purified by flash column chromatography (ethyl acetate/hexane 7:3) to give 1-allyloxycarbonyl-2-hydroxymethyl-4-t-butoxycarbonylthiopyrrolidine as a colourless oil (63%): NMR (CDCl$_3$) 1.5(s, 9H); 1.68(br s, 1H); 2.5(m, 1H); 3.25(dd, 1H); 3.7(m, 3H; 4.08(m, 2H); 4.6(br d, 2H); 5.3(m, 2H); 5.95(m, 1H). M/S CI (M+H)$^+$=318.

e) A solution of the product from d) above (4.82 mMol) in tetrahydrofuran (5 ml) was treated with triphenyl phosphine (7.41 mMol), phthalimide (7.40 mMol) and diethylazodicarboxylate (7.23 mMol). The reaction was allowed to stay at ambient temperature for 18 hours. The solvent was removed by evaporation and the residue purified by flash column chromatography (hexane:ethylacetate 3:1) to give 1-allyloxycarbonyl-2-phthalimidomethyl-4-t-butoxycarbonylthiopyrrolidine as a colourless oil (94%): NMR (DMSO-d$_6$ at 100° C.) 1.45(s,9H); 1.77(m,1H); 2.57(m, 1H); 3.16(dd,1H); 3.70(m,2H); 3.95(m,2H); 4.31(m,3H); 5.1(m,2H); 5.75(m,1H); 7.81(s,4H): M/S +ve FAB (M+H)$^+$=447.

f) To a stirred solution of the product from e) (15 mMol) in ethanol (100 ml) was added hydrazine hydrate (30 mMol) and the solution was stirred at reflux under argon for 2 hours. The mixture was filtered, evaporated and taken into ethyl acetate. The partial solution was washed with aqueous NaCl dried over Na$_2$SO$_4$ and evaporated. The product was isolated by medium pressure chromatography on silica, eluting with 10% MeOH/CH$_2$Cl$_2$ (U.V. detector 226 mm). The product was taken into ethyl acetate and washed with water to remove residual MeOH dried over Na$_2$SO$_4$ and evaporated to give the product as a viscous oil (75%): NMR (CDCl$_3$/CD$_3$COOD) 1.49(s,9H); 1.74(m, 1H); 2.65(m,1H); 3.29(m,3H); 3.71(m,1H); 4.14(m,2H); 4.61(d,2H); 5.28(m,2H); 5.92(m,1H): M/S CI (M+H)$^+$=317.

Preparation of Compounds (G)

3,4-Diallyloxy-5-bromobenzoic acid was prepared as follows:

Methyl 3,4-dihydroxy-5-bromobenzoate (49 g, see Chem. Abs., 89:2327 g) and $K_2CO_3$ (92 g) were placed in a flask in acetone (500 ml). Allyl bromide (49 ml) was slowly added to the mixture, which was stirred at room temperature for 5 days. After filtration, solvent was evaporated, the residue taken up in ethyl acetate, washed with water, and dried ($MgSO_4$). Evaporation of the solvent gave methyl 3,4-diallyloxy-5-bromobenzoate (65 g): NMR (DMSO-$d_6$) 3.86 (s, 3H); 4.67 (m, 4H); 5.20–5.53 (m, 4H); 5.95–6.19 (m, 2H); 7.54 (d, 1H); 7.73 (d, 1H).

Crude ester (65 g) was dissolved in methanol (400 ml), and treated with aqueous sodium hydroxide (40 ml, 10.5N). After reflux overnight, methanol was evaporated, the aqueous residue diluted with water, and acidified with conc. HCl. The white precipitate was filtered off, and dissolved ill ethyl acetate. A water layer was separated, and the organic layer dried over $MgSO_4$. Filtration and evaporation gave as a white solid 3,4-diallyloxy-5-bromobenzoic acid (59 g): NMR ($CDCl_3$) 4.67 (m, 4H); 5.42–5.51 (m, 4H); 6.00–6.21 (m, 2H); 7.56 (d, 1H); 7.94 (d, 1H), 11.33 (s,1 1H).

3,4,5-Triallyloxybenzoic acid was prepared as follows:

Ethyl gallate (7.92 g, commercially available, Fluka), and $K_2CO_3$ (27.6 g) in DMF (40 ml) were treated with allyl bromide (13.5 ml) as above, to give ethyl 3,4,5-triallyloxybenzoate acid (14 g): NMR ($CDCl_3$) 1.49 (t, 3H); 4.35 (q, 2H); 4.62 (m, 6H); 5.15–5.48 (m, 6H); 6.00–6.28 (m, 3H); 7.29 (s, 1H). This crude ester was hydrolysed essentially as above to give 3,4,5-triallyloxybenzoic acid (10.4 g): NMR ($CDCl_3$) 4.64 (m, 6H); 5.15–5.51 (m, 6H); 6.00–6.20 (m, 3H); 7.35 (s, 1H).

3,4-Diallyloxy-5-cyanobenzoic acid was prepared as follows:

3,4-Dihydroxy-5-cyanobenzoic acid, (see GB 2 200 109) was converted, essentially as above, to allyl 3,4-diallyloxy-5-cyanobenzoate: NMR ($CDCl_3$) 4.63 (m, 2H); 4.77–4.87 (m, 4H); 5.23–5.51 (m, 6H); 5.92–6.18 (m, 3H); 7.76 (d, 1H); 7.86 (d, 1H). This ester was hydrolysed as above to give 3,4-diallyloxy-5-cyanobenzoic acid: NMR (DMSO-$d_6$) 4.72–4.84 (m, 4H); 5.23–5.51 (m, 4H); 5.93–6.18 (m, 2H); 7.79 (s, 2H).

3,4-Diallyloxy-5-methanesulphonylbenzoic acid was prepared as follows:

Morpholine (2.09 g), which had been dried over molecular sieves, and dry THF (40 ml) were cooled under argon to −700°, and n-butyllithium (1.6M) in hexane (15 ml) was run in.

3-Bromo-4,5-dimethoxybenzaldehyde (4.9 g) in THF (30 ml) was added over 10 minutes and the mixture cooled to 31 75° . Further n-butyllithium (20 ml) was then added, and the mixture stirred at −75° for 80 minutes, before adding dimethyldisulphide (2.7 g) by syringe. The mixture was stirred for 1.5 hours, allowing the temperature to rise to ambient, then treated with an aqueous solution of ammonium chloride (50 ml) and the organic layer separated. The aqueous layer was extracted with ethyl acetate and the combined organic layers washed with brine, and dried over $NaSO_4$. Crude product was purified by chromatography on silica, eluting with 10% ethyl acetate in hexane, to give 3,4-dimethoxy-5-methylthiobenzaldehyde (3.4 g): NMR ($CDCl_3$): δ2.49 (s, 3H); 3.94 (s, 3H); 3.96 (s, 3H); 7.25 (d, 1H); 7.28 (d, 1H); 9.89 (s, 1H).

3,4-Dimethoxy-5-methylthiobenzaldehyde (5.1 g) was dissolved in acetone (200 ml), and treated with a solution of potassium permanganate (12.1 g) in water (350 ml) diluted with acetone (350 ml). After stirring 16 hours at ambient temperature, the mixture was treated with an excess of 5% aqueous sodium metabisulphite and organics extracted into ethyl acetate. The combined organic layers were washed with brine, dried ($MgSO_4$) and evaporated to give a white solid. This was dissolved in methanol (400 ml) and further oxidised by treatment with oxone (potassium monopersulphate, 4.7 g) in water (50 ml) at 5° for 3 hours. Solvent was evaporated and the residue was taken up in ethyl acetate, washed with brine, dried over $MgSO_4$, and evaporated to give 5-methanesulphonyl-3,4-dimethoxybenzoic acid (6.3 g) as a white solid: NMR: δ3.26 (s, 3H); 3.98 (s, 3H); 4.01 (s, 3H); 7.87 (d, 1H); 8.02 (d, 1H).

5-Methanesulphonyl-3,4-dimethoxybenzoic acid (6 g) was suspended in dichloromethane (90 ml) by stirring at room temperature under argon. A solution of boron tribromide (1M) in dichloromethane (51 ml) was added in two equal portions, immediately, and after 20 minutes, and stirring was continued for 16 hours. The mixture was poured carefully into a mixture of crushed ice (200 g) and $NaHCO_3$ (30 g), stirred for 30 minutes, and acidified with 12N hydrochloric acid to pH 1. The mixture was extracted with several portions of warm ethyl acetate to give after evaporation 5-methanesulphonyl-3,4-dimethoxybenzoic acid as a solid (5.2 g): NMR (DMSO-$d_6$): δ3.25 (s, 3H); 7.62 (d, 1H); 7.82 (d, 1H).

5-Methanesulphonyl-3,4-dimethoxybenzoic acid (5.3 g) was dissolved in DMF (50 ml), anhydrous $K_2CO_3$ (15.8 g) added, followed by allyl bromide (11.05 g), and the whole stirred under argon for 48 hours. Solvent was evaporated, the residue acidified to pH 6 with an aqueous solution of $NaH_2P_4$ and organics extracted into ethyl acetate. The combined organic extracts were washed with brine and evaporated. The product was purified by chromatography on silica eluting with 1.5% ethyl acetate in dichloromethane to give allyl 3,4-diallyloxy-5-methanesulphonylbenzoate (4.2 g), mp 78°–80°, NMR ($CDCl_3$): δ3.25 (s, 3H); 4.69 (dt, 4H); 4.79–4.84 (m, 4H); 5.27–5.53 (m, 6H); 5.93–6.29 (m, 3H); 7.85 (d, 1H); 8.26 (d, 1H).

This ester (5.8 g) was dissolved in ethanol (100 ml), treated with an aqueous solution of potassium hydroxide (1.11 g) in water (10 ml) and heated at reflux for 16 hours, The solvent was evaporated and the residue acidified to pH 1 with 2N hydrochloric acid. The organics were extracted into ethyl acetate and the extracts washed with brine and dried over $MgSO_4$ to give 3,4-diallyloxy-5-methanesulphonylbenzoic acid (5 g), mp 163°–16420 , NMR (DMSO-$d_6$): δ3.32 (s, 3H); 4.78 (m, 4H); 5.26–5.51 (m, 4H); 6.01–6.23 (m, 2H); 7.84 (d, 1H); 7.98 (d, 1H); 13.37 (br, 1H).

3,4-Diallyloxy-6-cyanobenzoic acid was prepared as follows:

To a suspension of allyl 3,4-diallyloxy-6-aminobenzoate * (16 mmol) in ethanol (50 ml) was added a solution of potassium hyroxide (48 mmol) in water (2ml). The mixture was heated at reflux for 40 minutes. The solution was partially evaporated at reduced pressure, acidified with acetic acid and extracted with ethylaceate. The organic layer was washed with water, a saturated solution of sodium chloride, dried ($MgSO_4$) and decolourised with charcoal. Evaporation of the solvent gave 3,4-diallyloxy-6-aminobenzoic acid as a sandy solid. NMR (DMSO-d$_6$): 4.5(m,4H); 5.33 ,4H); 6.60(s,1H); 7.3(s,1H): M/S +ve FAB (M+H)hu +=250.

* [Allyl 3,4-diallyloxy-6-aminobenzoate was prepared by acetylation of 2-amino-4,5-dimethoxybenzoic acid to give 2-acetamido-4,5-benzoic acid. Removal of the methyl groups with BBr$_3$ to give 2-acetamido-4,5-dihydroxybenzoic acid. Alkylation with allyl bromide to give allyl 2-acetamido-4,5-diallyloxybenzoate and removal of the acyl group with concentrated hydrochloric acid in methanol].

A solution of sodium nitrate (2.0 mmol) in water (1 ml) was slowly added to a stirred suspension of 3,4-diallyloxy-6-aminobenzoic acid (1.8 mmol) in a 2N aqueous solution of hydrochloric acid (5 ml) at 0° C. Water (10 ml) was added and the reaction mixture stirred for 30 minutes. The pH of the mixture was adjusted to pH8 by the addition of solid potassium carbonate. A solution of copper (I) cyanate was prepared by dissolving copper (I) chloride (2.25 mmol) in a solution of sodium cyanate (6.3 mmol) in water (5 ml). This was added to the rection mixture. The resulting mixture was slowly warmed to 50° C. and stirred for 20 minutes. The mixture was then heated on a steam bath for 20 minutes and acidified with a 5N aqueous solution of hydrochloric acid. This solution was extracted with ethyl acetate. The organic phase was washed with a 5N aqueous solution of hydrochloric acid and a saturated aqueous solution of sodium chloride. The organic phase was then extracted with a saturated aqueous solution of sodium hydrogen carbonate. The aqueous phase was acidified and extracted with ethyl acetate. This organic phase was washed with a saturated aqueous solution of sodium chloride and dried (MgSO$_4$). The solvent was evaporated to give 3,4-diallyloxy-6-cyanobenzoic acid as a light orange solid. NMR (DMSO-d$_6$): 4.73(m,4H); 5.35(m,4H); 6.04(m,2H); 7.48(s,1H); 7.57(s,1H): M/S CI (M+H)+=260.

4,5-Di-(allyloxy)-2-(2,5-dioxopyrrolidin-1-yloxycarbonyl)-N,N-dimethylbenzamide was prepared as follows:

Dimethyl 4,5-dihydroxyphthalate was alkylated with allylbromide/potassium carbonate in acetone (Reetz et al, Berichte, 112, 2209, 1979). The product was hydrolysed with sodium hydroxide in methanol to give the diacid. The diacid was heated with acetic anhydride to give 4,5-diallyloxyphthalic anhydride.

We claim:

1. A carbapenem compound of the formula (I)

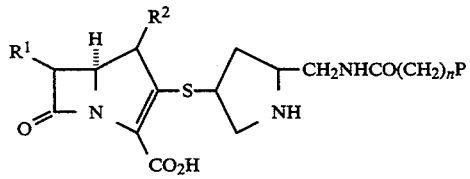

wherein:
R$^1$ is 1-hydroxyethyl, 1-fluoroethyl or hydroxymethyl;
R$^2$ is hydrogen or C$_{1-4}$alkyl;

n is zero or an integer 1 to 4; and
P is a benzene ring substituted by groups R$^3$ and R$^4$ which are ortho with respect to one another wherein R$^3$ and R$^4$ are independently hydroxy or an in vivo hydrolysable ester thereof;
or P is a group of the formula (II) or (III)

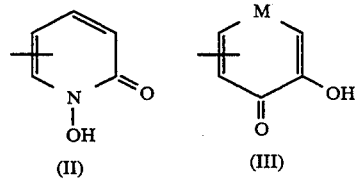

wherein
M is oxygen or a group NR$^5$ wherein R$^5$ is hydrogen or C$_{1-4}$alkyl;
ring P being optionally further substituted;
or a pharmaceutically acceptable salt or in vivo hydrolysable ester thereof.

2. A compound according to either claim 1 wherein R$^1$ is 1-hydroxyethyl.

3. A compound according to claim 1 wherein R$^2$ is hydrogen.

4. A compound according to claim 1 wherein P is a benzene ring substituted by groups R$^3$ and R$^4$ which are ortho with respect to one another wherein R$^3$ and R$^4$ are independently hydroxy or an in vivo hydrolysable ester thereof; the benzene ring being optionally further substituted.

5. A compound according to claim 1 wherein ring P is optionally further substituted by C$_{1-4}$alkyl, halo, hydroxy, hydroxyC$_{1-4}$alkyl, amino, nitro, C$_{1-4}$alkoxy, carboxyC$_{1-4}$alkyl, C$_{1-4}$alkanoylamino, N-alkyl-N-C$_{1-4}$alkanoylamino, trifluoromethyl, carboxy, carbamoyl, C$_{1-4}$alkylcarbamoyl, di-C$_{1-4}$alkylcarbamoyl, cyano, C$_{1-4}$alkanesulphonamido, C$_{1-4}$alkanoyl, C$_{1-4}$alkanoyloxy, C$_{1-4}$alkoxycarbonyl, C$_{1-4}$alkylthio, C$_{1-4}$alkanesulphinyl, C$_{1-4}$alkanesulphonyl, C$_{2-4}$alkenyl, hydroxyiminomethyl (HON=CH—), C$_{1-4}$alkoxyiminomethyl, aminosulphonyl, N-C$_{1-4}$alkylaminosulphonyl or di-[N-C$_{1-4}$alkyl]aminosulphonyl.

6. A compound according to claim 1 wherein ring P is optionally further substituted by fluoro, bromo, chloro, cyano, carboxymethyl, hydroxy, di-[N-methyl]carbamoyl, methanesulphonyl, di-[N-ethyl]aminosulphonyl or methoxycarbonyl.

7. A compound according to claim 1 of the formula (IV):

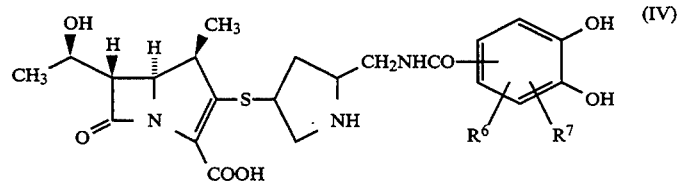

wherein R$^6$ and R$^7$ are independently hydrogen, halo, cyano, nitro, carboxy, carboxymethyl, hydroxy, methoxy, methoxyiminomethyl methanesulphonyl, di-[N-methyl]carbamoyl or di-[N-ethyl]aminosulphonyl.

8. A compound according to claim 7 wherein the benzene ring is substituted by the hydroxy groups in positions 3 and 4 relative to the amido linking group.

9. A compound according to claim 1 which is selected from:
(5R,6S,8R,2'S,4'S)-2-(2-(3,4-dihydroxybenzoylaminomethyl)pyrrolidin-4-ylthio)-6-(1-hydroxyethyl)carbapenem-3-carboxylic acid;
(5R,6S,8R,2'S,4'S)-2-(2-(5-bromo-3,4-dihydroxybenzoylaminomethyl)pyrrolidin-4-ylthio)-6-(1-hydroxyethyl)carbapenem-3-carboxylic acid;
(1R,8R,6S,8R,2'S,4'S)-2-(2-(5-cyano-3,4-dihydroxybenzoylaminomethyl)pyrrolidin-4-ylthio)-6-(1-hydroxyethyl)-1-methylcarbapenem-3-carboxylic acid;
(1R,8R,6S,8R,2'S,4'S)-2-(2-(5-hydroxy-3,4-dihydroxybenzoylaminomethyl)pyrrolidin-4-ylthio)-6-(1-hydroxyethyl)-1-methylcarbapenem-3-carboxylic acid;
(1R,8R,6S,8R,2'S,4'S)-2-(2-(6-carboxy-3,4-dihydroxybenzoylaminomethyl)pyrrolidin-4-ylthio)-6-(1-hydroxyethyl)-1-methylcarbapenem-3-carboxylic acid;
(1R,5R,6S,8R,2'S,4'S)-2-(2-(5-methylsulphonyl-3,4-dihydroxybenzoylaminomethyl)p idin-4-ylthio)-6-(1-hydroxyethyl)-1-methylcarbapenem-3-carboxylic acid;
(1R,8R,6S,8R,2'S,4'S)-2-(2-(6-di-(N-methyl)carbamoyl)-3,4-dihydroxybenzoylaminomethyl)pyrrolidin-4-ylthio)-6-(1-hydroxyethyl)-1-methylcarbapenem-3-carboxylic acid;
(1R,5R,6S,8R,2'S,4'S)-2-(2-(6-cyano-3,4-dihydroxybenzoylaminomethyl)pyrrolidin-4-ylthio)-6-(1-hydroxyethyl)-1-methylcarbapenem-3-carboxylic acid;
(1R,5R,6S,8R,2'S,4'S)-2-(2-(3,4-dihydroxybenzoylaminomethyl)pyrrolidin-4-ylthio)-6-(1-hydroxyethyl)-1-methylcarbapenem-3carboxylic acid; and
(1R,8R,6S,8R,2'S,4'S)-2-(2-(4,5-dihydroxypyridin-2-ylcarbonylaminomethyl)pyrrolidin-4-ylthio)-6-(1-hydroxyethyl)-1-methylcarbapenem-3-carboxylic acid;
or a pharmaceutically acceptable salt or in vivo hydrolysable ester thereof.

10. An antibacterial pharmaceutical composition which comprises a compound according to claim 1 and a pharmaceutically acceptable carrier.

11. A method of treatment of an infection by administering an antibacterially effective amount of a carbapenem compound of the formula (I) according to claim 1 to a patient in need thereof.

12. A compound of formula (V)

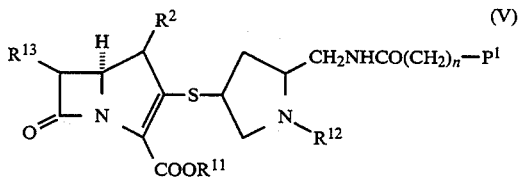

wherein:
$R^2$ is hydrogen or $C_{1-4}$alkyl;
$R^{13}$ is 1-hydroxyethyl, 1-fluorethyl, hydroxymethyl or 1-(protected hydroxy) ethyl;
$R^{11}$ is hydrogen or a carboxy protecting group;
$R^{12}$ is hydrogen or an amino protecting group;
n is zero or an integer 1 to 4;
$P^1$ is group P optionally protected with one or more hydroxy protecting groups wherein
P is a benzene ring substituted by groups $R^3$ and $R^4$ which are ortho with respect to one another wherein $R^3$ and $R^4$ are independently hydroxy or an in vivo hydrolysable ester thereof,
or P is a group of the formula (II) or (III)

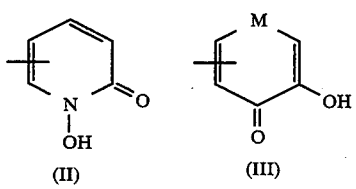

wherein
M is oxygen or a group $NR^5$ wherein $R^5$ is hydrogen or $C_{1-4}$alkyl, ring P being optionally further substituted.

* * * * *